(12) United States Patent
Yanmaele et al.

(10) Patent No.: US 6,291,435 B1
(45) Date of Patent: Sep. 18, 2001

(54) TREATMENT OF DIARRHEA CAUSED BY ENTEROPATHOGENIC ESCHERICHIA COLI

(75) Inventors: Rosa P. Yanmaele; Glen D. Armstrong, both of Edmonton (CA)

(73) Assignee: The Governs of the University of Alberta, Edmonton (CA)

( * ) Notice: Subject to any disclaimer, the term of this patent is extended or adjusted under 35 U.S.C. 154(b) by 0 days.

(21) Appl. No.: 09/517,079

(22) Filed: Mar. 1, 2000

Related U.S. Application Data

(60) Provisional application No. 60/123,033, filed on Mar. 4, 1999.

(51) Int. Cl.[7] .................................................... A61K 31/70
(52) U.S. Cl. .............................. 514/25; 514/53; 514/867; 536/55.1; 536/55.2; 536/17.2
(58) Field of Search ................................ 514/25, 53, 867; 536/55.1, 55.2, 17.2

(56) References Cited

U.S. PATENT DOCUMENTS 5,627,163 * 5/1997 Heerze et al. .
5,858,698 * 1/1999 Armstrong et al. .

FOREIGN PATENT DOCUMENTS

WO 95/21628 8/1995 (WO) .
WO 96/39189 12/1996 (WO) .
WO 97/49431 12/1997 (WO) .
WO 00/08467 2/2000 (WO) .

OTHER PUBLICATIONS

Vanmaele, Rosa P., L.D. Heerze, G. D. Armstrong. 1999. Role of lactosyl glycan sequences in inhibiting enteropathogenic *Escherichia coli* attachment. *Infect. and Immunity*. vol. 67, No. 7, pp. 3302–3307.

Vanmaele, Rosa P., L.D. Heerze, G.D. Armstrong. 1999. Role of lactosyl glycan sequences in inhibiting enteropathogenic *Escherichia coli* attachment. Abstracts of the General Meeting of the American Society for Microbiology. vol. 99. pp. 43.

Database WPI Derwent Publications Ltd., GB; AN 1999–100995. Vero toxin neutralizing agent. 1998. Abstract.

(List continued on next page.)

*Primary Examiner*—Gary Geist
*Assistant Examiner*—Devesh Khare
(74) *Attorney, Agent, or Firm*—Burns, Doane, Swecker & Mathis LLP

(57) ABSTRACT

This invention relates to compositions and methods useful to treat diarrhea, especially diarrhea and related conditions initiated or mediated by enteropathogenic *E. coli* (EPEC), using oligosaccharide compositions. This invention also relates to compositions and methods to reduce the virulence of an EPEC organism.

23 Claims, 8 Drawing Sheets

OTHER PUBLICATIONS

Heerze, L.D., M. A. Kelm, J.A. Talbot, G.D. Armstrong. 1994. Oligosaccharide sequences attached to an inert support (SYNSORB) as potential therapy for antibiotic–associated diarrhea and pseudomembranous colitis. J. of Infect. Dis. vol. 169. No. 6, pp. 1291–1296.

Database NIH/PUBMED: 2000. Enteropahtogeic *Escherichia coli.* Abstract.

Copy of Search Report from PCT/CA00/00218) dated Aug. 18. 2000.

AduBobie, J., G. Frankel, C. Bain, A. G. Goncalves, L. R. Trabulsi, G. Douce, S. Knutton, and G. Dougan. 1998. Detection of intimins alpha, beta, gamma, and delta, four intimin derivatives expressed by attaching and effacing microbial pathogens. J. Clin. Microbiol. 36:662–668.

Agin, T. S., and M. K. Wolf. 1997. Identification of a family of intimins common to *Escherichia coli* causing attaching–effacing lesions in rabbits, humans, and swine. Infect. Immun. 65:320–6.

Albert, M. J., K. Alam, M. Islam, J. Montanaro, A. S. Rahaman, K. Haider, M. A. Hossain, A. K. Kibriya, and S. Tzipori. 1991. Hafnia alvei, a probable cause of diarrhea in humans, Infect. Immun. 59:1507–1513.

Ashkenazi, S. 1994. A review of the effect of human milk fractions on the adherence of diarrheogenic *Escherichia coli* to the gut in an animal model. Isr. J. Med. Sci. 30:335–338.

Baldini, M. M., J. B. Kaper, M. M. Levine, D. C. A. Candy, and H. W. Moon. 1983. Plasmid–mediated adhesion in enteropathogenic *Escherichia coli.* J. Pediatr. Gastroenterol. Nutr. 2:534–538.

Baldwin, T. J., S. Knutton, R. Haigh, P. H. Williams, H. M. Palmer, A. Aitken, and S. P. Borriello. 1996. Hijacking host cell signal transduction mechanisms during infection with enteropathogenic *Escherichia coli.* Biochem. Soc. Trans. 24:552–558.

Beebakhee, G., M. Louie, J. De Azavedo, and J. Brunton. 1992. Cloning and nucleotide sequence of the eae gene homologue from enterohemorrhagic *Escherichia coli* serotype O157:H7. FEMS Microbiol. Lett. 70:63–68.

Chart, H., and B. Rowe, 1989. The outer membrane protein of enteropathogenic *Escherichia coli,* described as the 'localised adherence factor', is OmpF and probably not involved in adhesion to HEp-2 cells. FEMS Microbiol. Lett. 61:291–296.

Chart, H., S. M. Scotland, G. A. Willshaw, and B. Rowe. 1988. HEp-2 adhesion and the expression of a 94 kDa outer–membrane protein by strains of *Escherichia coli* belonging to enteropathogenic serogroups. J. Gen. Microbiol. 134:1315–1321.

Clausen, C. R., and D. L. Christie. 1982. Chronic diarrhea in infants caused by adherent enteropathogenic *Escherichia coli* J. Pediatr. 100:358–61.

Cravioto, A., R. J. Gross, S. M. Scotland, and B. Rowe. 1979. An adhesive factor found in strains of *Escherichia coli* belonging to the traditional infantile enteropathogenic serotypes. Curr. Microbiol. 3:95–99.

Cravioto, A., A. Tello, H. Villafan, J. Ruiz, S. del Vedovo, and J. R. Neeser. 1991. Inhibition of localized adhesion of enteropathogenic *Escherichia coli* to HEp-2 cells by immunoglobulin and oligosaccharide fractions of human colostrum and breast milk. J. Infect. Dis. 163:1247–1255.

Deibel, C., S. Kramer, T. Chakraborty, and F. Ebel. 1998. EspE, a novel secreted protein of attaching and effacing bacteria, is directly translocated into infected host cells, where it appears as a tyrosine–phosphorylated 90 kDa protein. Mol. Microbiol. 28:463–474.

Donnenberg, M. S. 1995. Enteropathogenic *Escherichia coli,* p. 709–726. In M. J. Blaser, P. D. Smith, J. I. Ravdin, H. B. Greenberg, and R. L. Guerrant (ed.), Infections of the Gastrointestinal Tract. Raven Press, Ltd., New York.

Donnenberg, M. S., J. A. Giron, J. P. Nataro, and J. B. Kaper. 1992. A plasmid–encoded type IV fimbrial gene of enteropathogenic *Escherichia coli* associated with localized adherence. Mol. Microbiol. 6:3427–3437.

Donnenberg, M. S., S. B. Calderwood, A. Donohue Rolfe, G. T. Keusch, and J. B. Kaper. 1990. Construction and analysis of TnphoA mutants of enteropathogenic *Escherichia coli* unable to invade HEp–2 cells. Infect. Immun. 58:1565–1571.

Eden, C. S., R. Freter, L. Hagberg, R. Hull, H. Leffler, and G. Schoolnik. 1982. Inhibition of experimental ascending urinary tract infection by an epithelial cell–surface receptor analogue. Nature. 298:560–562.

Finne, J., M. E. Breimer, G. C. Hansson, K. A. Karlsson, H. Leffler, J. F. G. Vliegenthart, and H. van Halbeek. 1989. Novel polyfucosylated N–linked glycopeptides with blood group A, H, X, and Y determinants from human small intestinal epithelial cells. J. Biol. Chem. 264:5720–5735.

Frankel, G., D. C. A. Candy, P. Everest, and G. Dougan. 1994. Characterization of the C–terminal domains of intimin–like proteins of enteropathogenic and enterohemorrhagic *Escherichia coli, Citrobacter freundii,* and *Hafina alvei,* Infect. Immun. 62:1835–1842.

Frankel, G., O. Lider, R. Hershkoviz, A. P., Mould, S. G. Kachalsky, D. C. A. Candy, L. Cahalon, M. J. Humphries, and G. Dougan. 1996. The cell–binding domain of intimin from enteropathogenic *Escherichia coli* binds to beta1 integrins. J. Biol. Chem. 271:20359–20364.

Francis, D. H., J. E. Collins, and J. R. Duimstra. 1986. Infection of gnotobiotic pigs with an *Escherichia coli* O157:H7 strain associated with an outbreak of hemorrhagic colitis. Infect. Immun. 51:953–956.

Geyid, A., J. Fletcher, B. A. Gashe, and Ljungh. 1996. Invasion of tissue culture cells by diarrhoeagenic strains of *Escherichia coli* which lack the enteroinvasive inv gene. FEMS Immunol. Med. Microbiol. 14:15–24.

Giron, J. A., A. S. Y. Ho, and G. K. Schoolnik. 1993. Characterization of fimbriae produced by enteropathogenic *Escherichia coli.* J. Bacteriol. 175:7391–7403.

Giron, J. A., A. S., Ho, and G. K. Schoolnik. 1991. An inducible bundle–forming pilus of enteropathogenic *Escherichia coli.* Science. 254:710–713.

Haigh, R., T. Baldwin, S. Knutton, and P. H. Williams. 1995. Carbon dioxide regulated secretion of the EaeB protein of enteropathogenic *Escherichia coli.* FEMS Microbiol. Lett. 129:63–67.

Hicks, S., G. Frankel, J. B. Kaper, G. Dougan, and A. D. Phillips. 1998. Role of intimin and bundle–forming pili in enteropathogenic *Escherichia coli* adhesion to pediatric intestinal tissue in vitro. Infect. Immun. 66:1570–1578.

Idota, T., and H. Kawakami. 1995. Inhibitory effects of milk gangliosides on the adhesion of *Escherichia coli* to human intestinal carcinoma cells. Biosci. Biotechnol. Biochem. 59:69–72.

Jagannatha, H. M., U. K. Sharma, T. Ramaseshan, A. Surolia, and T. S. Balganesh. 1991. Identification of carbohydrate structures as receptors for localised adherent enteropathogenic *Escherichia coli* Microb. Pathog. 11:259–268.

Jarvis, K. G., J. A. Giron, A. E. Jerse, T. K. McDaniel, M. S. Donnenberg, and J. B. Kaper. 1995. Enteropathogenic *Escherichia coli* contains a putative type III secretion system necessary for the export of proteins involved in attaching and effacing lesion formation. Proc. Natl. Acad. Sci. USA. 92:7996–8000.

Jerse, A. E., W. C. Martin, J. E. Galen, and J. B. Kaper. 1990. Oligonucleotide probe for detection of the enteropathogenic *Escherichia coli* (EPEC) adherence factor of localized adherent EPEC. J. Clin. Microbiol. 28:2842–2844.

Jerse, A. E., and J. B. Kaper. 1991. The eae gene of enteropathogenic *Escherichia coli* encodes a 94–kilodalton membrane protein, the expression of which is influenced by the EAF plasmid. Infect. Immun. 59:4302–4309.

Jerse, A. E., J. Yu, B. D. Tall, and J. B. Kaper. 1990. A genetic locus of enteropathogenic *Escherchia coli* necessary for the production of attaching and effacing lesions on tissue culture cells. Proc. Natl. Acad. Sci. USA. 87:7839–7843.

Karch, H., J. Heesemann, R. Laufs, H. P. Kroll, J. B. Kaper, and M. M. Levine. 1987. Serological response to type 1–like somatic fimbriae in diarrheal infection due to classical enteropathogenic *Escherichia coli* Microb. Pathog. 2:425–434.

Karlsson, K. A. 1998. Meaning and therapeutic potential of microbial recognition of host glycconjugates. Mol. Microbiol. 29:1–11.

Kenny, B., and B. B. Finlay. 1995. Protein secretion by enteropathogenic *Escherichia coli* is essential for transducing signals to epithelial cells. Proc. Natl. Acad. Sci. USA. 92:7991–7995.

Kenny, B., A. Abe, M. Stein, and B. B. Finlay. 1997. Enteropathogenic *Escherichia coli* protein secretion is induced in response to conditions similar to those in the gastrointestinal tract. Infect. Immun. 65:2606–2612.

Kenny, B., R. DeVinney, M. Stein, D. J. Reinscheid, E. A. Frey, and B. B. Finlay. 1997. Enteropathogenic *E. coli* (EPEC) transfers its receptor for intimate adherence into mammalian cells. Cell. 91:511–520.

Kenny, B., L. C. Lai, B. B. Finlay, and M. S. Donneberg. 1996. EspA, a protein secreted by enteropathogenic *Escherichia coli*, is required to induce signals in epithelial cells. Mol. Microbiol. 20:313–323.

Knutton, S., M. M. Baldini, J. B. Kaper, and A. S. McNeish, 1987. Role of plasmid–encoded adherence factors in adhesion of enteropathogenic *Escherichia coli* to HEp–2 cells. Infect. Immun. 55:78–85.

Knutton, S., I. Rosenshine, M. J. Pallen, I. Nisan, B. C. Neves, C. Bain, C. Wolff, G. Dougan, and G. Frankel. 1998. A novel EspA–associated surface organelle of enteropathogenic *Escherichia coli* involved in protein translocation into epithelial cells. EMBO J. 17:2166–2176.

Knutton, S., J. AduBobie, C. Bain, A. D. Phillips, G. Dougan, and G. Frankel, 1997. Down regulation of intimin expression during attaching and effacing enteropathogenic *Escherichia coli* adhesion. Infect. Immun. 65:1644–1652.

Knutton, S., T. Baldwin, P. H. Williams, and A. S. McNeish. 1989. Actin accumulation at sites of bacterial adhesion to tissue culture cells: basis of a new diagnostic test for enteropathogenic and enterohemorrhagic *Escherichia coli*. Infect. Immun. 57:1290–1298.

Laemmli, U. K. 1970. Cleavage of structural proteins during the assembly of the head of bacteriophage T4. Nature. 227:680–5.

Lai, L. C., L. A. Wainwright, K. D. Stone, and M. S. Donnenberg. 1997. A third secreted protein that is encoded by the enteropathogenic *Escherichia coli* pathogenicity island is required for transduction of signals and for attaching and effacing activities in host cells. Infect. Immun. 65:2211–2217.

Lee, C. A. 1997. Type III secretion systems: machines to deliver bacterial proteins into eukaryotic cells? Trends Microbiol. 5:148–56.

Lemieux, R. U., D. R. Bundle, and D. A. Baker. 1975. The properties of a "synthetic" antigen related to the human blood–group Lewis a. J. Am. Chem. Soc. 97:4076–4083.

Levine, M. M., E. J. Bergquist, D. R. Nalin, D. H. Waterman, R. B. Hornick, C. R. Young, and S. Sotman. 1978 *Escherichia coli* strains that cause diarrhoea but do not produce heat–labile or heat–stable enterotoxins and are non–invasive. Lancet. i:1119–1122.

Moon, H. W., S. C. Whipp, R. A. Argenzio, M. M. Levine, and R. A. Giannella. 1983. Attaching and effacing activities of rabbit and human enteropathogenic *Escherichia coli* in pig and rabbit intestines. Infect. Immun. 41:1340–1351.

Mouricourt, M. 1991. Swine and cattle enterotoxigenic *Escherichia coli*—mediated diaharrea. Development of therapies based on inhibiton of bacteria–host interactions. Eur. J. Epidemiol. 7:588–604.

Prieto, P. A., R. D. Larsen, M. Cho, H. N. Rivera, A. Shilatifard, J. B. Lowe, R. D. Cummings, and D. F. Smith. 1997. Expression of human H–type alpha1,2–fucosyltransferase encoding for blood group H(O) antigen in Chinese hamster ovary cells. J. Biol. Chem. 272:2089–2097.

Puente, J. L., D. Bieber, S. W. Ramer, W. Murray, and G. K. Schoolnik. 1996. The bundle–forming pili of enteropathogenic *Escherichia coli:* Transcriptional regulation by environmental signals. Mol. Microbiol. 20:87–100.

Rosenshine, I., M. S. Donnenberg, J. B. Kaper, and B. B. Finlay. 1992. Signal transduction between enteropathogenic *Escherichia coli* (EPEC) and epithelial cells: EPEC induces tyrosine phosphorylation of host cell proteins to initiate cytoskeletal rearrangement and bacterial uptake. EMBO J. 11:3551–3560.

Rosenshine, I., S. Ruschkowski, and B. B. Finlay. 1996. Expression of attaching effacing activity by enteropathogenic *Escherichia coli* depends on growth phase, temperature, and protein synthesis upon contact with epithelial cells. Infect. Immun. 64:966–973.

Rosenshine, I. S. Ruschkowski, M. Stein, D. J. Reinscheid, S. D. Mills, and B. B. Finlay. 1996. A pathogenic bacterium triggers epithelial signals to form a functional bacterial receptor that mediates actin pseudopod formation. EMBO J. 15:2613–2624.

Rothbaum, R., A. J. McAdams, R. Giannella, and J. C. Partin. 1982. A clinicopathologic study of enterocyte–adherent *Escherichia coli:* a cause of protracted diahrrea in infants. Gastroenterology. 83:441–454.

Scaletsky, I. C., S. R. Milani, L. R. Trabulsi, and L. R. Travassos. 1988. Isolation and characterization of localized adherence factor of enteropathogenic *Escherichia coli*. Infect. Immun. 56:2979–2983.

Scaletsky, I. C. A., M. L. Silva, and L. R. Trabulsi. 1984. Distinctive patterns of adherence of enteropathogenic *Escherichia coli* to HeLa cells. Infect. Immun. 45:534–536.

Schauer, D. B., and S. Falkow. 1993. Attaching and effacing locus of a *Citrobacter freundii* biotype that causes transmissible murine colonic hyperplasia. Infect. Immun. 61:2486–2492.

Scotland, S. M., J. E. Richmond, and B. Rowe. 1983. Adhesion of enteropathogenic strains of *Escherichia coli* (EPEC) to HEp–2 cells is not dependent on the presence of fimbriae. FEMS Microbiol. Lett. 20:191–195.

Simon, P. M., P. L. Goode, A. Mobasseri, and D. Zopf. 1997. Inhibition of *Helicobacter pylori* binding to gastrointestinal epithelial cells by sialic acid–containing oligosaccharides. Infect. Immun. 65:750–757.

Sohel, I., J. L. Puente, S. W. Ramer, D. Bieber, C. Y. Wu, and G. K. Schoolnik. 1996. Enteropathogenic *Escherichia coli:* identification of a gene cluster coding for bundle–forming pilus morphogenesis. J. Bacteriol. 178:2613–2628.

Stevens, M.G., et al. 1993 "Comparative analysis using MTT and XTT in colorimetric assays for quantitating bovine neutrophil bactericidal activity", *J. Immun. Meth.,* 157:225–231.

Stone, K. D., H.Z. Zhang, L. K. Carlson, and M. S. Donnenberg. 1996. A cluster of fourteen genes from enteropathogenic *Escherichia coli* is sufficient for the biogenesis of a type IV pilus. Mol. Microbiol. 20:325–337.

Tzipori, S., I. K. Wachsmuth, C. Chapman, R. Birden, J. Brittingham, C. Jackson, and J. Hogg. 1986. The pathogenesis of hemorrhagic colitis caused by *Escherichia coli* O157:H7 in gnotobiotic piglets. J. Infect. Dis. 154:712–6.

Ulshen, M. H., and J. L. Rollo. 1980. Pathogenesis of *Escherichia coli* gastroenteritis in man—another mechanism. N. Engl. J. Med. 302:99–101.

Vanmaele, R. P., M. C. Finalyson, and G, D. Armstrong. 1995. Effect of enteropathogenic *Escherichia coli* on adherent properties of Chinese hamster ovary cells. Infect. Immun. 63:191–198.

Vanmaele, R. P., and G. D. Armstrong. 1997. Effect of carbon source on localized adherence of enteropathogenic *Escherichia coli*. Infect. Immun. 65:1408–1413.

Vuopio–Varkila, J., and G. K. Schoolnik. 1991. Localized adherence by enteropathogenic *Escherichia coli* is an inducible phenotype associated with the expression of new outer membrane proteins. J. Exp. Med. 174:1167–1177.

Wadstrom, T., R. A. Adegbola, S. B. Baloda, A. Ljungh, S. K. Sethi, and Y. R. Yuk. 1986. Non–haemagglutinating fimbriae of enteropathogenic *Escherichia coli* (EPEC) Zentralbl. Bakteriol. Hyg. 261:417–424.

Wanke, C. A. 1995. Enteropathogenic and enteroaggregative strains of *Escherichia coli:* clinical features of infection, epidemiology, and pathogenesis. Curr. Clin. Top. Infect. Dis. 15:230–252.

Yakubu, D. E., D. C. Old, and A. Tavendale. 1991. Production of a mannose–resistant fibrillar haemagglutinin by strains of *Escherichia coli* of EPEC serotype O111:H2. FEMS Microbiol. Lett. 65:233–238.

Yu, J., and J. B. Kaper. 1992. Cloning and characterization of the eae gene of enterohaemorrhagic *Escherichia coli* O157:H7. Mol. Microbiol. 6:411–417.

Zhang, J.P., and S. Normark. 1996. Induction of Gene Expression in *Escherichia coli* after Pilus–Mediated Adherence. Science: 273:1234–1236.

Zhang, H. Z., and M. S. Donnenberg. 1996. DsbA is required for stability of the type IV pilin of enteropathogenic *Escherichia coli*. Mol. Microbiol. 21:787–797.

Zopf, D., and S. Roth. 1996. Oligosaccharide anti–infective agents. Lancet. 347:1017–1021.

* cited by examiner

Linear Equation: y = 0.002x - 0.259
Correlation Coefficient: r = 0.997

US 6,291,435 B1

TREATMENT OF DIARRHEA CAUSED BY ENTEROPATHOGENIC ESCHERICHIA COLI

CROSS-REFERENCE TO RELATED APPLICATIONS

This application claims priority under 35 U.S.C. §119(e) to U.S. application Ser. No. 60/123,033 filed Mar. 4, 1999, the disclosure of which is incorporated herein by reference.

FIELD OF THE INVENTION

This invention relates to treatment of diarrhea, particularly diarrhea caused by enteropathogenic Escherichia coli (EPEC). More specifically, the invention concerns compositions and methods which may be used to prevent EPEC infection or ameliorate symptoms caused by EPEC infection.

BACKGROUND OF THE INVENTION

Enteropathogenic Escherichia coli (EPEC) is a significant cause of diarrhea world-wide, with disease occuring most frequently in developing countries [1–3]. In these countries, disease occurs regularly in hospitals and clinics, as well as in the general community. EPEC outbreaks in developed countries, on the other hand, usually consist of sporadic, isolated incidents which are localized to neonatal nurseries of hospitals or day-care centers. Infants less than 6 months of age are most often affected, although EPEC is also capable of causing disease in children and adults. The transmission of EPEC infections is thought to occur primarily by the fecal-oral route as a result of contact with infected individuals or with contaminated surfaces or food. The isolation of EPEC from asymptomatic individuals has led to speculation that some individuals may be carriers who can also spread infection.

Clinical symptoms of EPEC infection in children consist of diarrhea which varies in duration (days to months) and severity [3,4]. In addition to profuse watery stool, symptoms include dehydration, fever, vomiting and weight loss. In protracted or severe cases, disease is often associated with the delayed growth of children, metabolic acidosis (decrease in blood pH resulting from a loss of bicarbonate [5,6]) and, in extreme cases, death. Adults participating in volunteer studies of EPEC infection displayed symptoms similar to those observed in children, but of shorter duration.

Results of volunteer studies indicate that, at least in adults, a relatively large infectious dose of organisms is required to produce symptoms which typically occur 7 to 16 h after infection [1,7]. For ethical reasons, similar information for EPEC infection in children is not available. It is speculated however, that a much lower number of organisms is required to infect children since transmission frequently occurs in hospitals or day-care facilities [1]. Treatment for EPEC infection usually consists of rehydration therapy and, if necessary, nutritional supplementation. Antibiotics are often used to treat EPEC infection though their overall effectiveness is uncertain [3].

Biopsies from children infected with EPEC reveal that the bacteria predominantly colonize the small intestine, although the large intestine can also be involved, presumably due to bacterial overgrowth [2,4,8,9]. The primary histopathological consequence of colonization is the atrophy or degeneration of microvilli at sites of bacterial attachment and the intimate association of bacteria with pedestal-like structures formed by host epithelial cells (e.g., enterocytes). This characteristic effect is referred to as an attaching and effacing (A/E) lesion [4,9–11]. Other features include the deterioration of the terminal web (apical region beneath microvilli consisting of cytoskeletal proteins which are physically associated with the central actin filaments of microvilli) of enterocytes, a reduction in mucosal thickness, and a general disordered arrangement of enterocytes. Bacteria are rarely found within intestinal epithelial cells or in the lamina propria, suggesting that EPEC are not invasive. An infiltration of inflammatory cells into the lamina propria of the intestine is also frequently observed during EPEC infection.

Clinical symptoms caused by EPEC result from bacterial attachment to the intestinal epithelium. Donnenberg and Kaper proposed a model in which EPEC attachment involves a three-step process [12]. The initial step consists of initial, non-intimate attachment of bacteria as microcolonies to epithelial cells. Next, the bacteria secrete several proteins which induce signal transduction pathways in epithelial cells. These signals initiate cytoskeletal rearrangement followed by the effacement of microvilli of host cells. In the final stage of attachment, cytoskeletal components are organized to form cup-like pedestal structures which partially surround adherent organisms. The latter steps of effacement and intimate attachment result in the characteristic A/E lesions associated with EPEC [11]. A modified version of this model has recently been suggested by Hicks, et al. In their model, three-dimensional microcolonies of EPEC are thought to develop after, not before, intimate attachment has occurred [13].

Since adherence is an important factor in EPEC pathogenesis, considerable research has been performed to identify bacterial and eukaryotic cell structures involved in attachment. So far, two bacterial structures have been relatively well characterized. The first, bundle-forming pili (BFP), are associated with the initial, non-intimate attachment of EPEC as microcolonies to discrete sites on epithelial cells, a pattern which is referred to as localized adherence (LA) [14,23,27]. Scanning electron micrographs of LA EPEC revealed that BFP are involved in mediating inter-bacterial linkages within microcolonies. Whether the BFP also function as adhesins for EPEC binding to epithelial cells remains to be resolved, however, since these structures appear to mediate bacterial binding to HEp-2 cells but not to human intestinal tissue in organ culture [13,27,47]. A second bacterial protein involved in attachment is intimin [36,48]. This protein is necessary for a later stage of EPEC attachment in that it focuses host cell cytoskeletal components beneath adherent bacteria to form A/E lesions [33].

Cravioto, et al. initially demonstrated that EPEC adhered to HEp-2 cells in greater numbers than other groups of E. coli studied, and that this adherence was not due to type I fimbriae [14]. Type I pili are structures which are expressed with similar frequency by pathogenic and non-pathogenic Escherichia coli (E. coli) strains, and whose binding is inhibited by mannose [15]. Subsequent investigations resulted in several different structures being proposed as EPEC adhesins. These structures included unidentified non-fimbrial [16] and fimbrial adhesins [17–19], fimbriae with N-terminal sequence homology to the fimbriae of uropathogenic and diffusely-adhering E. coli [20], and a 32 kDa outer membrane protein [21] (later reported to be OmpF [22]). However, the observation that EPEC grown in tissue culture medium attached to epithelial cells in a LA pattern [23,24], and that this phenotype was encoded by a large EPEC adherence factor (EAF) plasmid [25], led to the identification of a structure required for this pattern of binding.

In 1991, Giron, et al. described unqiue rope-like structures, termed BFP, [26] which appeared by scanning electron microscopy, to intercourse between bacteria to form microcolonies, and to attach the microcolonies to HEp-2 cells. Their role in attachment was supported by observations that antibodies raised against purified BFP partially inhibited EPEC attachment, and mutants lacking the EAF plasmid did not express BFP. The structural subunit of BFP is BfpA [52].

Following the effacement of microvilli, the formation of actin pedestals characteristic of A/E lesions requires the bacterial protein intimin [33,35,36]. Intimin is a 94 kDa outer membrane protein encoded by the eae gene of the locus of enterocyte effacement (LEE). The expression of this protein is necessary to focus host cytoskeletal proteins which accumulate beneath the organisms into pedestals, and for bacteria to become intimately associated (less than 10 mn separation) with this structure [11]. Based on serological and genetic techniques, EPEC intimins have been classified into three groups [35,37,38]. Despite variations in antigenicity and gene sequences, however, the proteins are believed to be functionally equivalent. The greatest diversity among these proteins occurs within the C-terminus, which is also thought to be the host cell binding domain [39].

Recently, Knutton, et al. demonstrated that intimin expression is down-regulated following the formation of A/E lesions [40]. This may indicate that, once bacteria have achieved their goal of becoming intimately associated with host cells, continued expression of this protein is no longer required in order to remain attached. Alternatively, since intimin is immunogenic [41], this may be a mechanism by which EPEC are able to evade the host immune response.

EPEC receptors on host eukaryotic cells are less well characterized than bacterial structures involved in attachment. Recently, the receptor for intimin, which was previously believed to be a host cell protein (Hp90), was also shown to be a protein secreted by EPEC [31–34]. This protein, referred to as Tir (translocated intimin receptor) (78 kDa) or *E. coli* secreted protein E (EspE) [25], is translocated into host cells where it becomes phosphorylated at tyrosine residues and then serves as the receptor for intimin [31,50]. Frankel, et al. reported that intimin may also bind to $\beta_1$ integrins [49].

Investigations into the regulation of EPEC virulence factor expression were initiated by the observations of Vuopio-Varkila and Schoolnik that the LA phenotype of EPEC was promoted by growing the bacteria in a defined medium [24]. Since then, both environmental and genetic factors that regulate the expression of EPEC virulence factors have been described.

In the report of Vuopio-Varkila and Schoolnik, which described the positive effect of tissue culture growth medium on EPEC attachment, the increase in attachment correlated with higher levels of BFP expression [24]. Subsequently, several reports identified growth conditions that are optimal for the expression of EPEC virulence factors. Specific media components which were found to affect the expression of BFP or Esps include: calcium (BfpA and Esps), ammonium (BfpA), and $FeNO_3$ (Esps) [44,45]. Results from our laboratory indicated that EPEC binding to HEp-2 cells and the expression of BfpA and intimin were also affected by carbon source [42]. Regarding general environmental conditions, the secretion of Esps was dependent on the osmolarity and pH of the tissue culture medium [43,44,75]. Growth at 37° C. was also optimal for the expression of BfpA and Esps, and for the formation of A/E lesions [44–46]. Since the expression of different EPEC virulence factors is affected by the same environmental condition(s), these factors may be coordinately regulated [44].

Studies by several research groups have implicated carbohydrate structures as host cell receptors for EPEC. In studies where soluble compounds were used to inhibit attachment, N-acetyl-galactosamine [21], $GM_3$ gangliosides [27], or fucosylated tetra- and pentasaccharides [28] and the GalNAcβ(1→4)Gal portion of asialo-$GM_1$ and asialo-$GM_2$ structures [2] were found to be implicated in EPEC attachment to eukaryotic cells, based on their inhibition of EPEC binding (Table 1). These structures, excluding $GM_3$ gangliosides, presumably inhibited initial attachment since inhibition was measured as a decrease in the numbers of LA EPEC bound to epithelial cells. Alternatively, when glycolipids were layered onto thin layer chromatography plates, EPEC preferentially recognized the GalNAcβ(1→4)Gal portion of asialo-$GM_1$ and asialo-$GM_2$ sequences [29]. These studies also suggested that the sequences were involved in initial attachment, since LA-negative mutants did not bind to these sequences. In addition to these results, work performed in our laboratory suggested that EPEC recognize lactosamine sequences on eukaryotic cells. We examined EPEC LA to Chinese hamster ovary cells or mutants of these cells which express altered oligosaccharide structures on their surface. Results of these studies suggested that asialo-lactosamine sequences on N-linked glycoproteins were sufficient for EPEC binding. Our results also supported a role for O-linked glycoproteins or glycolipids in attachment [30].

TABLE 1

Oligosaccharide Sequences Proposed to be Involved in EPEC Binding

| Oligosaccharide | [a]Inhibitory Sequence |
|---|---|
| N-acetylgalactosamine | GalNAc [21] |
| difucosyllactose | Fucα(1→2)Galβ(1→4)[Fucα(1→3)]Glc [28] |
| lacto-N-fucopentaose isomers | Fucα(1→2)Galβ(1→3)GlcNAcβ(1→3)Galβ(1→4)Glc<br>Galβ(1→3)[Fucα(1→4)]GlcNAcβ(1→3)Galβ(1→4)Glc;<br>Galβ(1→4)[Fucα(1→3)]GlcNAcβ(1→3)Galβ(1→4)Glc [28] |
| asialo $GM_1$ | [b]Galβ(1→3)<u>GalNAcβ(1→4)Galβ</u>(1→4)Glcβ(1→1)cer [29] |
| asialo $GM_2$ | [b]<u>GalNAcβ(1→4)Galβ</u>(1→4)Glc(1→1)cer [29] |
| $GM_3$ | Siaα(2→3)Galβ(1→4)Glcβ(1→1)cer [27] |
| lactosamine of N-linked glycoproteins | Galβ(1→3,4)GlcNAc [30] |
| O-linked glycoproteins or glycolipids | not known [30] |

TABLE 1-continued

Oligosaccharide Sequences Proposed to be Involved in EPEC Binding

| Oligosaccharide | [a]Inhibitory Sequence |
|---|---|

[a]N-acetylgalactosamine = GalNAc; fucose = Fuc; galactose = Gal; N-acetylglucosamine = GlcNac; glucose = Glc; Sia = sialic acid; ceramide = cer
[b]Underlined portion of sequence proposed to be inhibitory Several reports suggest that EPEC recognize lactosyl structures on epithelial cells. However, additional carbohydrate groups (i.e., sialic acid and fucose) are frequently attached to these core structures. While our previous results using CHO cell Lec mutants indicated that EPEC do not require sialic acid in order to bind, the importance of fucose in these interactions was not addressed since CHO cells do not express certain fucosylated glycans [51].

In view of the above, there is a need for a compound which would treat diarrhea and related symptoms caused by EPEC. A preferred compound would be administered noninvasively, such as orally, and would attenuate the virulence of EPEC organisms which express virulence factors such as BFP and intimin.

SUMMARY OF THE INVENTION

The invention provides compositions and methods for the treatment of diarrhea initiated or mediated by enteropathogenic *E. coli* (EPEC). The invention also provides compositions and methods for the treatment or amelioration of diarrhea and associated symptoms initiated or mediated by binding of EPEC to host cells in the gastrointestinal tract.

In one aspect, the invention provides a method to treat diarrhea and related conditions initiated or mediated by EPEC in a subject, which method comprises administering to a subject in need of such treatment an effective amount of a composition comprising an oligosaccharide sequence which reduces the virulence of EPEC. In particular, oligosaccharide sequences attached to a pharmaceutically acceptable support are provided.

In a further aspect, the invention provides a method to reduce the virulence of an EPEC organism, which method comprises contacting an EPEC organism which expresses virulence factors with an effective amount of a composition comprising an oligosaccharide sequence, wherein said oligosaccharide causes at least a 20% decrease in localized adherence of said organism.

In yet a further aspect, the invention provides a pharmaceutical composition useful for treating diarrhea and related conditions initiated or mediated by enteropathogenic *E. coli*, which composition comprises an oligosaccharide sequence which reduces the virulence of EPEC. In particular, oligosaccharide sequences attached to a pharmaceutically acceptable support are provided.

DETAILED DESCRIPTION OF THE INVENTION

A. Definitions

Figure 1:
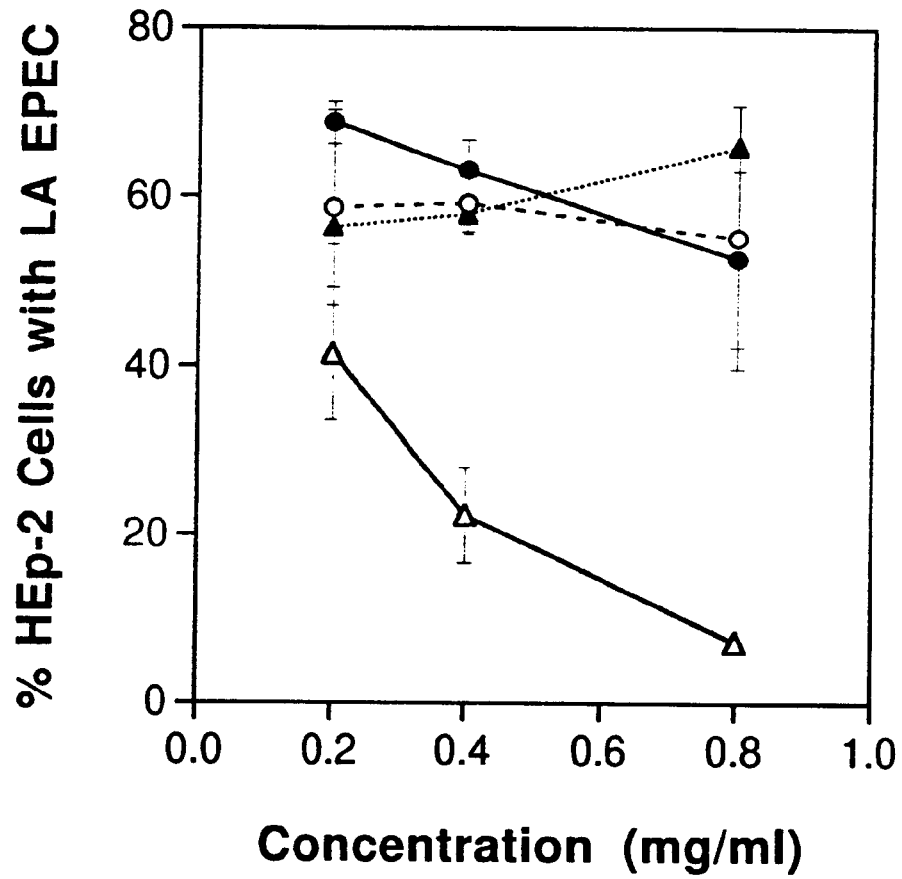
FIG. 1 illustrates the concentration dependent inhibition of EPEC localized adherence (LA) using various oligosaccharides.

As used herein the following terms have the following meanings:

The term "diarrhea" refers to profuse watery stool. This diarrhea may commonly be caused by enteropathogenic *E. coli* (EPEC).

The term "biocompatible" refers to chemical inertness with respect to human tissues or body fluids. Biocompatible materials are non-sensitizing.

The term "compatible linker arm" refers to a moiety which serves to space the oligosaccharide structure from the biocompatible support and which is bifunctional, wherein one functional group is capable of binding to a reciprocal functional group of the support and the other functional group is capable of binding to a reciprocal functional group of the oligosaccharide structure. Compatible linker arms preferred in the present invention are non-peptidyl spacer arms.

The term "oligosaccharide" means saccharides comprising 1 to about 20 saccharide moieties. Saccharide derivatives may also be used as saccharide moieties included in the term oligosaccharide.

The term "support" refers to an inert material to which the oligosaccharide sequences may be bound, either directly or via a compatible linker arm. Where use is in vivo, the support will be biocompatible.

The terms "reduce the virulence", "reduction of virulence", "attenuate" or "attenuate the virulence" mean that expression of virulence factors and/or localized adherence of the EPEC organism is reduced. For example, a pharmaceutical composition which reduces the virulence of an EPEC organism reduces the localized adherence of the EPEC organism by at least about 20%, as measured by in vitro assay.

The term "virulence factor" refers to any factor found in or secreted by an organism which initiates, mediates or is involved in the disease process. Virulence factors include, but are not limited to, toxins and molecules involved in attachment to host cells.

For the purpose of this application, all sugars are referenced using conventional three letter nomenclature. All sugars are assumed to be in the D-form unless otherwise noted, except for fucose, which is in the L-form. Further all sugars are in the pyranose form.

B. Synthesis

Chemical methods for the synthesis of oligosaccharide structures can be accomplished by methods known in the art. These materials are generally assembled using suitably protected individual monosaccharides. The specific methods employed are generally adapted and optimized for each individual structure to be synthesized.

In general, the chemical synthesis of all or part of an oligosaccharide glycoside first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature.

We have found that synthetic oligosaccharide sequences covalently attached to a biocompatible support, e.g., bovine serum albumin (BSA), may be used to reduce virulence of EPEC. These glycoconjugate compositions are useful to treat diarrhea and related conditions initiated or mediated by EPEC.

The supports to which the oligosaccharide structures of the present invention may be bound or immobilized include a wide variety of biocompatible materials known in the art. Proteins such as BSA may be used. Water soluble biocompatible polymers such as hydrogels, carboxymethyl celluloses, synthetic polymers, and the like are useful. In particular, these supports are useful for delivery to the gut, especially prolonged delivery. When non-absorbable are preferred, such supports may be soluble or insoluble, so long as they are not absorbed by the body.

Solid supports are particularly useful for certain applications. Such solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferably the solid supports have a particle size of from about 10 to 500 microns for in vivo use. In particular, particle sizes of 100 to 200 microns are preferred.

The oligosaccharide structure(s) may be covalently bound or noncovalently (passively) adsorbed onto the support so as to be immobilized to form an oligosaccharide-support structure. The covalent bonding may be via reaction between functional groups on the support and the compatible linker arm of the oligosaccharide structure. Linking moieties that are used in indirect bonding are preferably organic bifunctional molecules of appropriate length (at least one carbon atom) which serve simply to distance the oligosaccharide structure from the surface of the support.

Additionally, using a high density of oligosaccharide moieties on the support is particularly useful for attenuating EPEC.

C. Pharmaceutical Compositions

The methods of this invention are achieved by using pharmaceutical compositions comprising one or more oligosaccharide structures which reduce the virulence of enteropathogenic *E. coli.*

When used for oral administration, which is preferred, these compositions may be formulated in a variety of ways. They will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art. (See, e.g., *Remington's Pharm. Sci.,* 18th Ed., 1990.)

Compositions which may be mixed with semisolid foods such as enteral nutritional formulas, applesauce, ice cream or pudding may also be preferred. Formulations which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The composition itself may also be used without the addition of inert pharmaceutical carriers, particularly for use in capsule form.

Doses are selected to provide reduced virulence of EPEC in the gut of the affected patient. Preferred doses are from about 75–375 micromoles of oligosaccharide/kg body weight/day, more preferably about 150–300 micromoles of oligosaccharide/kg body weight/day. Administration is expected to be 1 to 4 times daily, for a period of one week or until clinical symptoms are resolved. The dose level and schedule of administration may vary depending on the particular oligosaccharide structure used and such factors as the age and condition of the subject.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 30 micromole oligosaccharide/ml.

D. Methodology

We have found that virulent EPEC may be attenuated by contacting them with certain oligosaccharide sequences. In particular, synthetic oligosaccharides covalently attached to supports via non-peptidyl compatible linker arms have been found to effectively inhibit LA and down-regulate EPEC virulence factors, thereby reducing the virulence of EPEC.

We have tested the ability of several oligosaccharide sequences attached to BSA via an 8-methoxylcarbonyloctyl (MCO) spacer arm to reduce the virulence of enteropathogenic *E. coli*. The structures tested are presented in Table 2.

TABLE 2

Oligosaccharide Sequences of BSA-Glycoconjugates

| Oligosaccharide | Structure |
|---|---|
| N-acetyllactosamine (LacNAc) | Galβ(1→4)GlcNAc |
| Lewis X (LeX) | Galβ(1→4)[Fucα(1→3)]GlcNAc |
| Lewis Y (LeY) | Fucα(1→2)Galβ(1→4)[Fucα(1→3)]GlcNAc |

As shown in FIGS. 1–3 and 8, the oligosaccharides tested varied in their ability to reduce localized adherence (LA) by at least about 20%.

The oligosaccharide sequences useful in the present invention include those which attenuate or reduce the virulence of EPEC. Attenuation or reduction of virulence of EPEC by an oligosaccharide is readily detectable by a simple in vitro test, as for example, set forth in Example 1 below. For the purposes of this invention, oligosaccharide sequences which reduce the virulence of EPEC means those compositions which inhibit LA of EPEC to HEp-2 cells by at least 20%, using the assay set forth in the Examples section.

Previous experiments with Chinese hamster ovary (CHO) cell Lec mutants demonstrated that EPEC bound to lactosamine sequences on epithelial cells (See U.S. Pat. No. 5,858,698, incorporated herein by reference). Although sialylated sequences were not necessary for recognition, since EPEC bound in similar numbers to wild-type CHO and Lec2 cells, these sequences might be involved in eukaryotic cell signaling. Our binding results were consistent with previous reports which suggested that lactosyl sequences were recognized by EPEC [27,28]. In contrast to earlier reports, however, using this model system we also found that lactosamine sequences of N-linked glycoproteins were receptors for EPEC. A role for these structures in initial, non-intimate attachment was suggested by the relatively short incubation period (1.5 h) required for a large number of EPEC to adhere to the CHO cells. (This incubation period was chosen since monolayer detachment occurred at later times). Intimin mediated attachment, in comparison, generally requires a co-incubation period greater than 3 h in order to observe significant levels of bacterial attachment [53].

To extend these results further, we performed binding inhibition experiments using synthetic, bovine serum albumin (BSA)-glycoconjugates to identify specific oligosaccharide sequences recognized by EPEC. When EPEC E2348/69 (O127:H6) [7] was used in these experiments, we found that N-acetyllactosamine (LacNAc)-BSA was the most effective inhibitor of bacterial attachment. These results supported our earlier results obtained with the CHO and Lec cell lines. Lewis X (LeX)-BSA also inhibited bacterial attachment, but to a lesser extent.

Our earlier results with CHO and Lec cells indicated that EPEC of three different serotypes recognized lactosamine sequences of epithelial cells. Therefore, we performed binding inhibition experiments to determine whether a similar pattern of inhibition would be observed for these strains. In contrast to results obtained with EPEC E2348/69, we found that EPEC O119:H6 was inhibited to the greatest extent by LeX-BSA, which was followed by LacNAc-BSA (FIG. 8). LacNAc-BSA was generally the most effective inhibitor of EPECO111:H2. These results show that EPEC may recognize more than one lactosyl structure.

For our studies with BSA-glycoconjugates, the specific carbohydrate structures were selected based on previous reports that N-linked glycoproteins of small intestinal epithelial cells of certain individuals consist primarily of lactosamine sequences in a β(1→4) linkage [54], and that EPEC preferentially recognized fucosylated lactosyl structures [28]. However, since intestinal cells can also express N-linked glycoproteins containing β(1→3)-linked lactosamine sequences [54] these oligosaccharides may also be more effective inhibitors of EPEC binding. A preferred oligosaccharide for use in the present invention would be a single carbohydrate structure that could inhibit the binding of a majority of EPEC isolates. Although the EPEC strains might display different sensitivities to inhibition by this structure, this sequence would reduce bacterial binding sufficiently to allow the host immune response to resolve the infection before clinical symptoms progress [55,56].

Results of the binding inhibition experiments show that carbohydrate sequences reduce EPEC attachment by causing a decrease in the expression of EPEC bundle-forming pili (BFP) and intimin. This novel effect has not been described previously. Our results that the expression of BPP and intimin are affected to different extents by LacNAc-BSA and LeX-BSA, respectively, suggests that the regulation of the expression of these adhesins varies based on environmental (or host) signals.

With respect to EPEC pathogenesis, our experimental results show that carbohydrate compounds may be used to treat EPEC infection. The advantage for using carbohydrate-based therapies, instead of treatments such as antibiotics, is that bacteria are unlikely to develop resistance to these compounds. From a bacterial perspective, once they bind to a carbohydrate structure, they "have found a host". Therefore, there is no selective pressure to modify their binding specificity. Although it is still possible that an organism with an altered adhesin could colonize the host, this occurrence is likely to be low [56].

In our experiments with the BSA-glycoconjugates, EPEC binding was inhibited when the glycoconjugates were used at a concentration of approximately 7–8 μM, depending on the glycoconjugate. These results resembled those recently reported by Simon et al. [76] in which *Helicobacter pylori* binding to epithelial cells in vitro was inhibited using micromolar concentrations of a multivalent conjugate consisting of 3'-sialyllactose conjugated to human serum albumin (20 mol/mol). The mechanism by which bacterial binding was inhibited in these experiments was not addressed. Although not described in detail, they also reported that the administration of this glycoconjugate to *Helicobacter pylori*-infected individuals caused a significant reduction in the number of gastric organisms as detected by a [$^{13}$C] breath test.

Our binding inhibition experiments demonstrate that a similar approach may be applied to altering the expression of other EPEC virulence factors, or analogous virulence factors of other enteric pathogens. Proteins exported by the type III secretory pathway of EPEC initiate signal transduction processes involved in the formation of A/E lesions [43,50,57]. The ability to alter the expression of these proteins is shown by results that demonstrate that their expression is also influenced by the plasma-encoded regulator (per) region [50], and by specific growth conditions which affect BFP and intimin levels [44]. If this is demonstrated, similar strategies might also be effective in altering protein secretion by type III pathways of other enteric pathogens, including, among others, *Helicobacter pylori*, Shigella spp, Salmonella spp, Yersinia spp, Campylobacter spp and enterovirulent *Escherichia coli* such as enterohemorrhagic *E. coli* (EHEC) [58,76]. Other possible targets for regulation by glycoconjugates are the intimins expressed by the human enteric pathogens (EHEC) [59,60] and *Hafnia alvei* [61] which also cause A/E lesions. Since intimins display the greatest diversity at their C-terminus [36,39,62–64] which is associated with binding specificity, however, it remains to be determined which oligosaccharide sequences will decrease the expression of intimin in these organisms.

Several different oligosaccharide sequences have been found to have the ability to reduce the virulence factors of EPEC. These sequences, and others that also reduce the virulence of EPEC, may be used to treat diarrhea and related conditions initiated or mediated by EPEC. Treatment may be accomplished by oral administration of compositions containing oligosaccharide sequences.

We have found that the ability to attenuate enteropathogenic *E. coli* is directly related to the oligosaccharide sequences which contact the EPEC. The results in FIGS. 1–5 and 8 show the effectiveness of the LacNAc, LeX and LeY oligosaccharides for EPEC virulence reduction. Accordingly, oligosaccharide sequences comprising Galβ(1→4)GlcNAc, Galβ(1→4)[Fucα(1→3)]GlcNAc and Fucα(1→2)Galβ(1→4)[Fucα(1→3)]GlcNAc will be useful in the methods and compositions of the invention.

In the present study, we used synthetic, multivalent BSA-glycoconjugates presenting either lactosamine (LacNAc) or fucosyllactosamine structures (LeX or LeY) to determine whether fucosylated glycan sequences had a role in EPEC attachment interactions [28]. EPEC E2348/69 was selected for these experiments since this strain is commonly used by other research groups to investigate EPEC pathogenesis [7,47,52,68]. Overall, we found that LacNAc-BSA was the most effective inhibitor of bacterial binding to HEp-2 cells, followed by LeX-BSA. LeY-BSA was the least effective inhibitor in our binding assays. Additional experiments performed to elucidate the manner in which these glycan structures inhibited binding led to the observation that incubation of EPEC E2348/69 with LacNAc-BSA and LeX-BSA caused decreases in the expression of BfpA and intimin, respectively. These results are significant because they revealed that the expression of BfpA and intimin, two proteins involved in EPEC attachment, were affected to varying extents by different glycoconjugates.

In previous experiments where carbohydrates were shown to inhibit bacterial attachment to tissue culture cells, it was presumed that these structures were host cell receptor analogs which acted as competitive antagonists of bacterial binding [69,70]. However, the results of our experiments, which indicated that the inhibition of EPEC E2348/69 binding by glycoconjugates correlated with a decrease in the expression of BfpA and intimin, suggest that the process of inhibition may be more complex. Recently, Knutton, et al. demonstrated that EPEC down-regulated intimin expression in the later stage(s) of attachment to HEp-2 cells [40]. A similar decrease in BFP levels was not observed during the same time period. Our results are similar to those of Knutton, et al. in that we also found that EPEC expressed lower levels of a protein(s) associated with attachment in response to environmental signals. Our results and those of Knutton, et al. suggest that intimin and BFP, to a degree, may be differentially regulated. Unlike their results, however, we found that specific glycoconjugates were able to mediate this effect independent of viable epithelial cells and that they affected BFP expression as well.

It appears that, in addition to the glycoconjugates possibly acting as competitive inhibitors of binding, their interaction with EPEC may stimulate bacteria to progress to later stages of the multi-step colonization process. This progression to a later stage is accompanied by a loss of structures required for attachment, and this reduces the ability of the bacteria to bind. Virulence factors of EPEC other than BFP and intimin would be similarly affected by treatment with oligosaccharides. Recently, Knutton, et al. demonstrated that EspA-associated surface structures also disappear from EPEC cell surfaces during the formation of A/E lesions [40]. Since this pattern of expression resembles that seen with intimin, this confirms that the secretion or expression of proteins involved in EPEC virulence [31,32,43,57,71–73] would also be affected by the interaction of bacteria with specific glycoconjugates.

An implication of the above model is that the glycoconjugates are analogs of epithelial cell receptors for EPEC. In our experiments, we used HEp-2 cells which are derived from laryngeal tissue. While results of investigations into the formation of A/E lesions with this cell line appear to parallel in vivo findings [17], recent results of Hicks, et al. suggest that the initial attachment of EPEC to HEp-2 cells differs from that observed with intestinal cells [13]. Specifically, Hicks, et al. reported that EPEC which expressed BFP, but not intimin, were able to attach to HEp-2 cells, but not to intestinal biopsy tissue. Whether LacNAc and LeX sequences used in our experiments mimic actual intestinal cell receptors in vivo remains to be determined. However, an important aspect of our results with the soluble BSA-glycoconjugates is that it is not necessary for the carbohydrate sequences on these structures to represent the natural host cell receptors for EPEC. The down-regulation of BfpA and intimin caused by soluble glycoconjugates, alone, reduces the ability of EPEC to bind to their relevant receptors in vivo. Thus, carbohydrate therapy can form the basis for a novel therapeutic intervention in this gastrointestinal disease.

E. EXAMPLES

The following materials and methods were used to perform the studies in the Examples that follow.

Reagents

All glycoconjugates consisted of chemically synthesized oligosaccharide sequences (Table 2) covalently conjugated to bovine serum albumin (BSA) through an 8-methoxycarbonyloctyl linker arm [65]. LacNAc-BSA and Lewis Y (LeY)-BSA were provided by O. Hindsgaul (University of Alberta, Edmonton, Alberta, Canada). LeX-BSA was purchased from the Alberta Research Council (Edmonton, Alberta, Canada). The incorporation of ligands into BSA (mol/mol) was determined by mass spectroscopy to be as follows: LacNAc-BSA (19:1), LeX-BSA (26:1) and LeY-BSA (17:1). All glycoconjugates were solubilized in phosphate-buffered saline (PBS) (5 mg/ml) and stored at −20° C. prior to use. Polyclonal rabbit anti-intimin [35] and anti-BfpA [66] antibodies were provided by J. B. Kaper and M. S. Donnenberg (University of Maryland School of Medicine, Baltimore, Md.), respectively. Rabbit anti-maltose-binding protein antibodies were purchased from New England Biolabs (Mississauga, Ontario, Canada).

Bacterial Strains

EPEC strain E2348/69 (O127:H6), a wild-type strain isolated from an infant with diarrhea [7], was provided by B.

B. Finlay (University of British Columbia, Vancouver, British Columbia, Canada). In each experiment, bacteria which were stored as frozen stock cultures at −70° C., were grown overnight at 37° C. on tryptic soy agar (Difco, Detroit, Mich.) plates. An isolated bacterial colony was then inoculated into tryptic soy broth (TSB) and incubated for 16 h, without shaking, at 37° C. under normal atmospheric conditions for use in experiments the following day.

Preparation of HEp-2 Cell Monolayers

HEp-2 cells (CCL-23) were obtained from the American Type Culture Collection (Rockville, Md.). The cells were grown at 37° C. in a humidified atmosphere of 5 % $CO_2$/ 95% air in minimal essential medium supplemented with 10% fetal bovine serum (FBS). Sub-confluent monolayers were prepared for the binding assays by disrupting HEp-2 monolayers with a solution of 0.25% (vol/vol) tissue culture grade trypsin in FC buffer (0.14 M NaCl, 5.0 mM KCl, 20.0 mM Tris-HCl, 5.0 mM Tris base, 0.5 mM EDTA; pH 7.2). After suspending the trypsinized HEp-2 cells in fresh tissue culture medium, approximately $7.5\times10^3$ cells in 150 μl of culture medium were added to individual wells, each well containing a 6 mm-diameter removable polystyrene disk (Biomedical Workshop, University of Alberta, Edmonton, Alberta, Canada) covering their bottoms, of 96-well tissue culture plates. The plates were then incubated in a $CO_2$ incubator until the following day.

EPEC Cell Binding Assay

For all experiments, EPEC E2348/69 was cultured in Dulbecco's modified Eagle medium (DMEM) (catalog no. 23800; Gibco, Burlington, Ontario, Canada) supplemented with 44 mM $NaHCO_3$, 40 μM phenol red, and 25 mM glucose, which was pre-equilibrated overnight in a $CO_2$ incubator [42]. FBS was not included in this culture medium. Prior to each experiment, 40 μl of the TSB-grown bacteria were inoculated into 4 ml DMEM in 15×75 mm borosilicate glass culture tubes which were then incubated for 1 h in a $CO_2$ incubator to induce the expression of EPEC virulence factors [24,42,46]. To determine the optimum concentration of glycoconjugates for the binding inhibition experiments, 32 μl of DMEM bacterial culture (approximately $4-5\times10^6$ colony forming units), and 52 μl DMEM (pre-equilibrated) were added to empty wells of a 96-well microtiter plate. Next, 16 μl of BSA-glycoconjugate solution (undiluted [5 mg/ml], or diluted 1:2 or 1:4 in PBS) was added to the wells to obtain final inhibitor concentrations of 0.8, 0.4, or 0.2 mg/ml, respectively. For all subsequent experiments, the volumes were adjusted such that 32 μl of DMEM bacterial culture, 56 μl DMEM and 12 μl of BSA-glycoconjugate (final concentration of 0.6 mg/ml) were added to wells of a 96-well plate. After mixing the contents of each well, the plate was incubated, without agitation, for 30 min at 37° C. in a $CO_2$ incubator. The entire contents from each of the wells were then transferred to wells containing sub-confluent HEp-2 cell monolayers from which the culture medium was first removed. This microtiter plate was incubated for an additional 30 min at 37° C. in the $CO_2$ incubator, after which time the cells were washed three times with PBS, fixed with methanol for 10 min, and stained with Giemsa stain for 20 min. The polystyrene disks were removed from the microtiter plate wells and EPEC adherence was monitored microscopically using the 100× objective lens. Depending on the number of microscopic fields required to view the entire area of the coverslip, 150–200 randomly chosen HEp-2 cells were examined. Those having attached microcolonies consisting of five or more bacteria were considered positive for LA EPEC [24].

Effect of Glycoconjugate Pre-incubation Period on Bacterial Attachment

EPEC E2348/69 was grown in DMEM for 1 h in a $CO_2$ incubator as described above. Next, 32 μl of bacterial culture and 56 μl DMEM were added to empty wells of a 96-well tissue culture plate. At this time, 12 μl BSA-glycoconjugate (final concentration of 0.6 mg/ml per well) was also added to sample wells for which the effect of pre-incubation with the BSA-glycoconjugate(s) was to be determined. After mixing the contents of each well, the plate was placed in a $CO_2$ incubator for 30 min. Next, 12 μl of BSA-glycoconjugate was added to the remaining, no preincubation, sample wells of the plate. The contents of all wells were then immediately transferred to wells of a 96-well microtiter plate containing sub-confluent HEp-2 cell monolayers grown on polystyrene disks, and the plate was incubated, without agitation, in a $CO_2$, 37° C. incubator for 30 min. The cells were then washed three times with PBS, fixed with methanol and stained with Giemsa stain. The percentage of HEp-2 cells with LA EPEC was determined as described in the previous section.

Determination of BfpA and Intimin Expression

After incubating EPEC E2348/69 in DMEM for 1 h to induce the expression of virulence factors, 96 μl of bacterial culture, 168 μl of DMEM and 36 μl of BSA-glycoconjugate (final concentration 0.6 mg/ml per well) were added to empty wells of a 48-well tissue culture plate. The plate was incubated in a $CO_2$ incubator for 1 h as described earlier, before transferring the contents of each well to microcentrifuge tubes. The bacteria were washed once with PBS by centrifugation and the resulting pellet was lysed in sodium dodecyl sulfate-polyacrylamide gel electrophoresis (SDS-PAGE) sample buffer containing 50 mM dithiothreitol [67]. Bacterial proteins were separated by SDS-PAGE (12.5% polyacrylamide) and electrophoretically transferred to an Immobilon-P membrane (Millipore, Bedford, Mass.).

Since different antibodies were used to detect specific proteins, the membrane was cut into 3 sections using the pre-stained molecular size standards as a guide. Nonspecific binding sites of the membranes were blocked with 5% skim milk (wt/vol) in PBS containing 0.05% Tween-20 (PBST) and the sections were incubated with various antibodies according to the recommendations of the supplier. The dilution for each antibody was as follows: anti-intimin (1:2000), anti-maltose-binding protein (1:10,000) and anti-BfpA (1:4000). After incubating the membranes with the antibodies for 2 h at room temperature, the membranes were washed three times with PBST before being incubated with goat anti-rabbit peroxidase-conjugated antibodies (1:18,000 dilution) for 1.5 h at room temperature. After washing again with PBST, followed by three washes with PBS, the membranes were incubated with the enhanced chemiluminescence (ECL) color development reagents according to the manufacturer's instructions (Amersham, Oakville, Ontario, Canada). Protein bands were visualized by exposing the membranes to Kodak X-Omat blue XB-1 film. Bands corresponding to intimin, maltose-binding protein and BfpA in each sample were analyzed using an LKB Ultroscan XL laser densitometer supplied with an LKB 2220 integrator.

Figure 6:
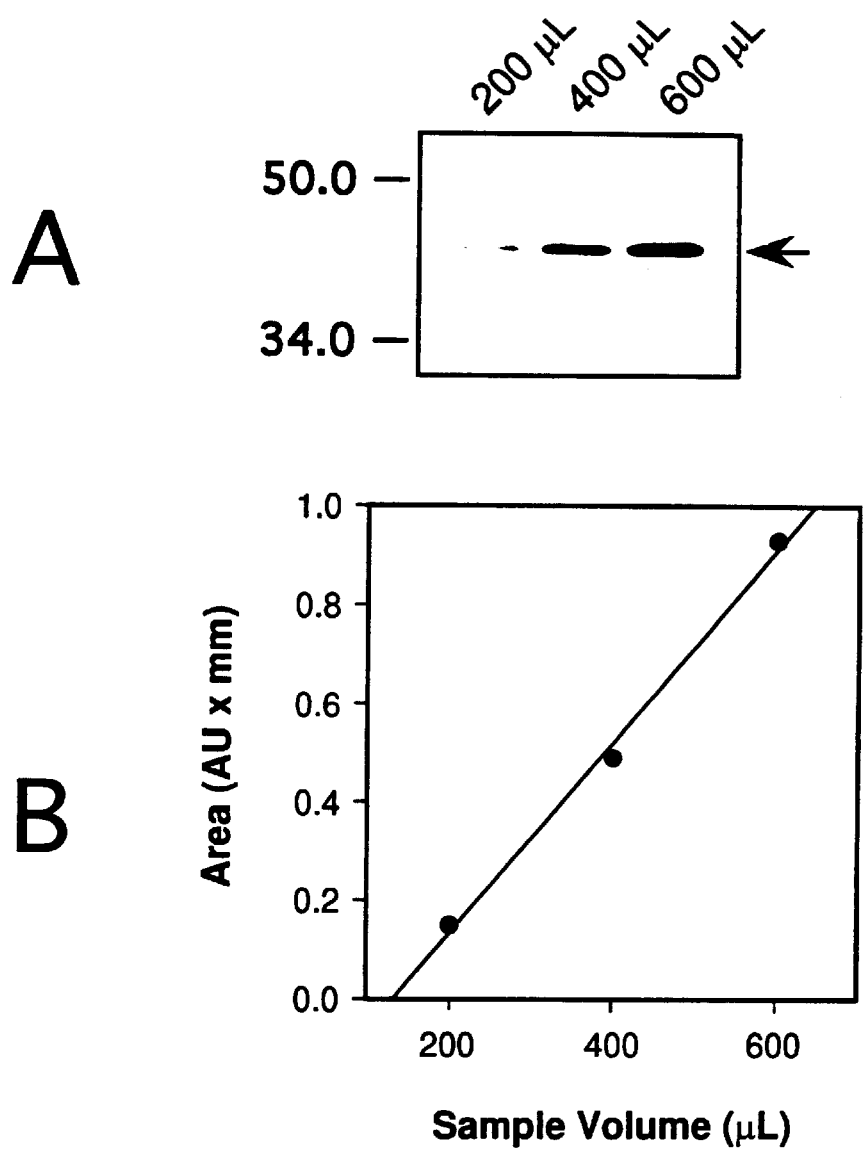
FIG. 6 illustrates the linearity of the enhanced chemiluminesence (ECL) response. This demonstrates that the assay used to measure protein gave linear results.

Studies were performed as follows to demonstrate the linearity of the ECL response. EPEC E2348/69 was grown in DMEM for 1 h as described earlier. Next, 2, 4 or 6× the volumes of bacterial culture, DMEM and BSA solution used in the binding inhibition experiments (final volumes of 200, 400 or 600 μl, respectively) were added to wells of a 48-well tissue culture plate. After incubating the plate for an additional 1 h in a $CO_2$ incubator, the bacteria were washed with PBS and separated by SDS-PAGE (12.5% polyacrylamide). Maltose-binding protein in each sample was then detected using the ECL detection system as described above and the levels were analyzed by densitometry. Plotting the data as shown in FIG. 6 indicated that the relationship between the amount of maltose-binding protein in each sample and the corresponding area determined by densitometry was linear (B).

The amounts of intimin and BfpA in each sample were normalized to the amount of the internal standard, maltose-binding protein, in each gel lane.

The following examples are offered to illustrate this invention and are not meant to be construed in any way as limiting the scope of this invention.

Example 1

Inhibition of EPEC LA by BSA-glycoconjugates

To identify possible carbohydrate sequences involved in EPEC E2348/69 binding to HEp-2 cells, we first cultured the bacteria in tissue culture medium to induce the expression of virulence factors. These bacteria were then pre-incubated with a specific glycoconjugate (Table 2) for 30 min at 37° C. Finally, the EPEC-glycoconjugate mixtures were added to HEp-2 cell monolayers for an additional 30 min to allow bacterial binding to occur.

Experiments to determine optimum BSA-glycoconjugate (s) concentration were performed as follows. After culturing EPEC E2348/69 in DMEM for 1 h in a $CO_2$ incubator, the bacteria, and various concentrations of BSA-glycoconjugate, were added to wells of a 96-well plate. The plate was then incubated in a $CO_2$ incubator for 30 min, after which time the contents of each well were transformed to wells of a 96-well plate containing subconfluent monolayers of HEp-2 cells grown on polystyrene coverslips. After incubating this plate in a $CO_2$ incubator for an additional 30 min, the cells were washed with PBS, fixed with methanol and stained with Giemsa stain. HEp-2 cells with adherent microcolonies consisting of five or more bacteria were considered positive for LA EPEC. Each data point shown in FIG. 1 represents the average of single determinations for a sample obtained in two independent trials. Error bars indicate the range in the data for each sample from both trials. BSA (-●-), LacNAc-BSA (-Δ-), LeX-BSA (---○---), and LeY-BSA (····568····).

Experiments were performed with various glycoconjugate concentrations. The results of these dose-dependent binding inhibition experiments demonstrated that LacNAc-BSA was the most effective inhibitor of EPEC E2348/69 attachment to HEp-2 cells (FIG. 1). This inhibition was concentration dependent over the range examined, 0.8, 0.4, or 0.2 mg/ml of LacNAc-BSA, resulting in approximately 87%, 65%, and 40% reduction, respectively, in EPEC LA to HEp-2 cells.

Based on the inhibitory effects observed with LacNAc-BSA in FIG. 1, we used the BSA-glycoconjugates at a final concentration of 0.6 mg/ml in all subsequent experiments.

Figure 2:
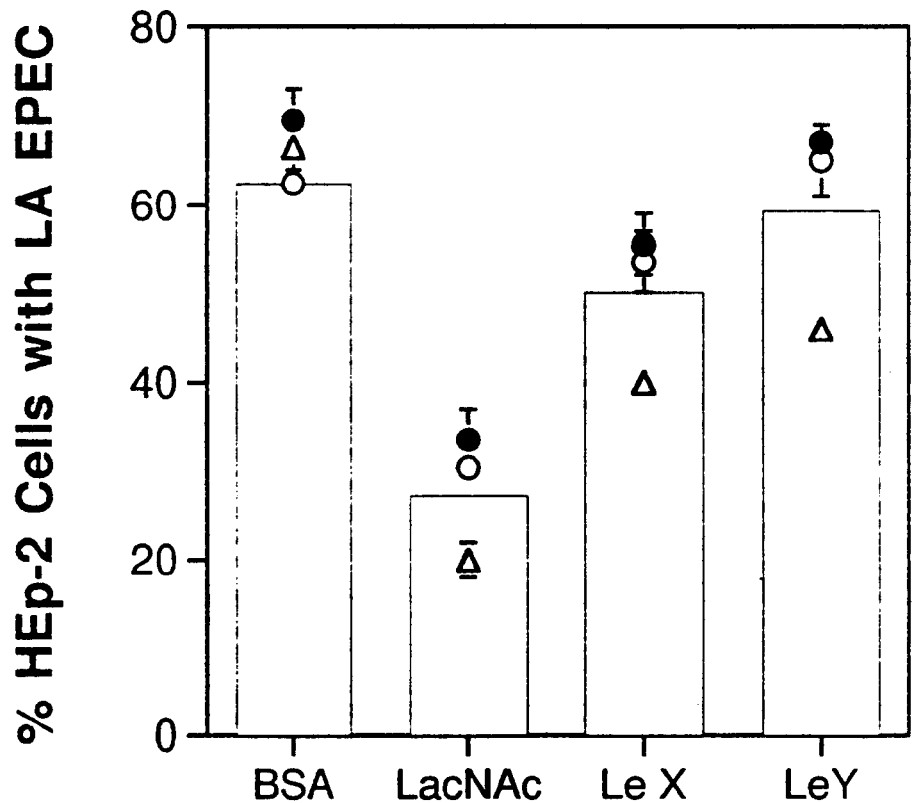
FIG. 2 demonstrates the effectiveness of various oligosaccharide-containing compositions to inhibit EPEC LA at a final concentration of 0.6 mg/ml.

To confirm the appropriateness of this concentration, three additional experiments were performed using EPEC E2348/69 (FIG. 2). Inhibition of EPEC E2348/69 binding to HEp-2 cells using BSA-glycoconjugates at a final concentration of 0.6 mg/ml per well was determined as follows. Experiments were performed essentially as described above, except that bacteria were incubated with BSA-glycoconjugates present at final concentrations of 0.6 mg/ml per well. After allowing the bacteria to bind to HEp-2 cells, the cells were washed with PBS, fixed with methanol and stained with Giemsa stain. The percentage of HEp-2 cells with LA EPEC was determined as described earlier. Data points for Trial 1 (●), Trial 2 (Δ) and Trial 3 (○) are indicated. Error bars for each of these points represent the range in values obtained for duplicate samples. The overlaying bar graph indicates the mean(s) of the data obtained in all three trials.

Figure 5:
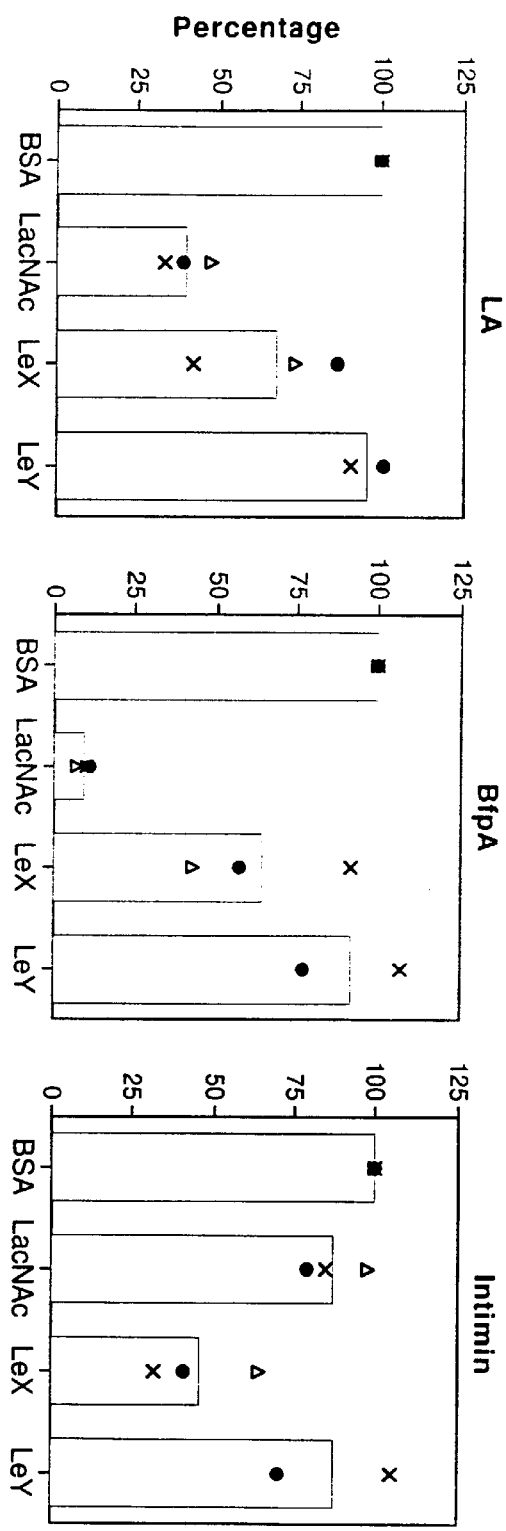
FIG. 5 demonstrates the relationship between EPEC binding and BFP or intimin levels.

Similar to the results presented in FIG. 1, FIG. 2 shows that LacNAc-BSA inhibited EPEC attachment to the greatest extent. LeX-BSA was the second most effective inhibitor of EPEC binding in these experiments, with LeY-BSA being the least effective. Comparable results were observed in later experiments performed in a similar manner (FIG. 5).

Additional control experiments confirmed that the inhibitory effect of these glycoconjugates was not due to a toxic effect of these compounds on the bacteria. The viability of EPEC after incubation with BSA-glycoconjugates was determined. EPEC E2348/69 was cultured in DMEM for 1 h in a $CO_2$ incubator as described above. Next, 32 μl of this culture, 56 μl of DMEM and 12 μl BSA-glycoconjugate were added to empty wells of a 96-well tissue culture plate. After incubating the plate in a $CO_2$ incubator for an additional 1 h, bacterial viability was determined using two methods. With the first method, the contents of each well were serially diluted in PBS and then plated onto TSA plates to determine the number of colony forming units (CFUs) in each sample (●).

Alternatively, since the number of CFU might be altered as a result of a glycoconjugate(s) inhibiting microcolony formation or causing the bacteria to aggregate, EPEC viability was also assessed using a modified XTT (sodium 3,3'-[1[(phenylamino)carbonyl]-3,4-tetrazolium]-bis(4-methoxy-6-nitro)benzene sulfonic acid hydrate) assay (Stevens, M. G., et al., "Comparative analysis using MTT and XTT in colorimetric assays for quantitating bovine neutrophil bactericidal activity", J. Immun. Meth., 157:225–231 (1993)). This assay is based on the ability of viable bacteria to reduce XTT to soluble, orange formazan. Color development, which can be measured at 450 nm, is proportional to the number of viable bacteria. For this method, after DMEM-grown bacteria were incubated with the glycoconjugates for 1 h, the contents of each well were transferred into Luria broth (1:50 dilution). These cultures were incubated for 4 h at 37° C., after which time 400 μl of each culture and 100 μl of a solution consisting of XTT (1 mg/ml) and Coenzyme Q (25 μg/ml) were transferred to wells of a 48-well plate. After incubating the plate at 37° C. for an additional 45 min, the cultures were transferred to microcentrifuge tubes and the bacteria were pelleted by centrifugation. The supernatant of each sample was collected and the $Abs_{450}$ for each was recorded (○).

Figure 7:
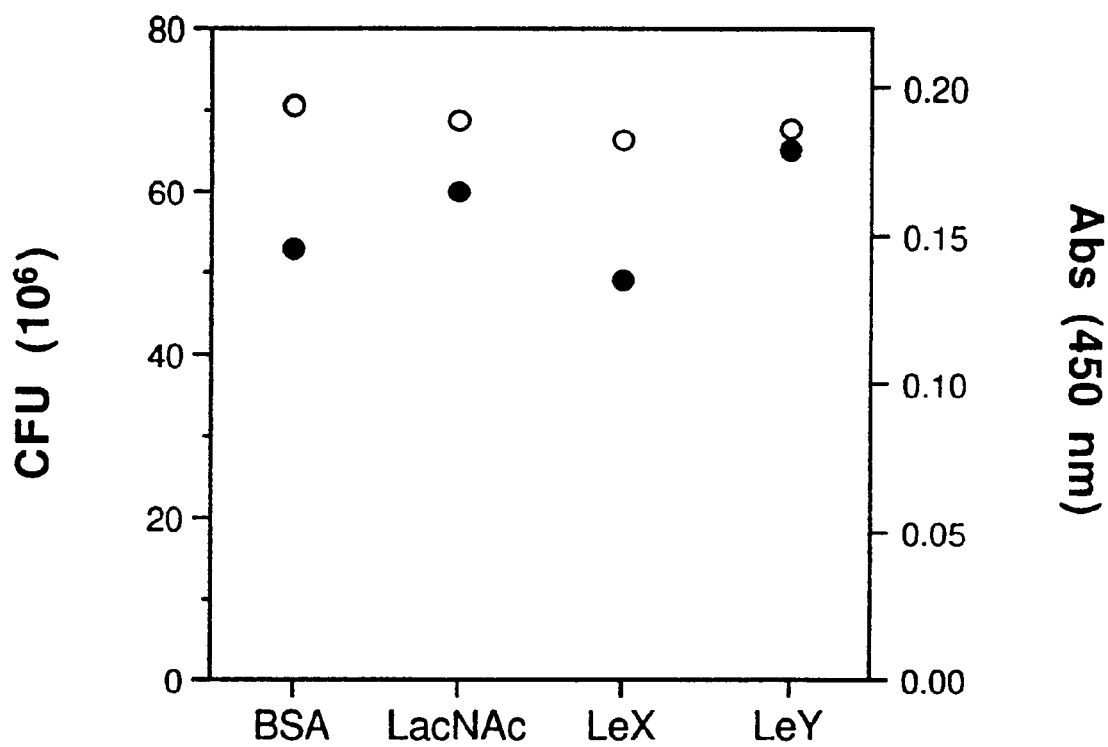
FIG. 7 demonstrates that glycoconjugate treatment of EPEC did not effect viability of the organisms as measured by colony forming units (CFU) or absorbance.

As can be seen in FIG. 7, neither the number of CFUs nor the $Abs_{450}$ was significantly affected by glycoconjugate treatment.

Example 2

Effect of Pre-Incubation on EPEC Attachment

The procedure used in the glycoconjugate inhibition binding experiments involved pre-incubating EPEC E2348/69 with various glycoconjugates for 30 min prior to adding the mixtures to the HEp-2 cell monolayers in order to allow sufficient time for the multivalent BSA-glycoconjugate inhibitors to occupy the maximum number of bacterial adhesin receptor binding sites prior to exposing the EPEC-glycoconjugate mixtures to the HEp-2 cells. To examine whether pre-incubation was necessary, experiments were performed in which the bacteria were either pre-incubated for 30 min with LacNAc-BSA before being added to the HEp-2 cells, or were added simultaneously with LacNAc-BSA to the monolayers.

Figure 3:
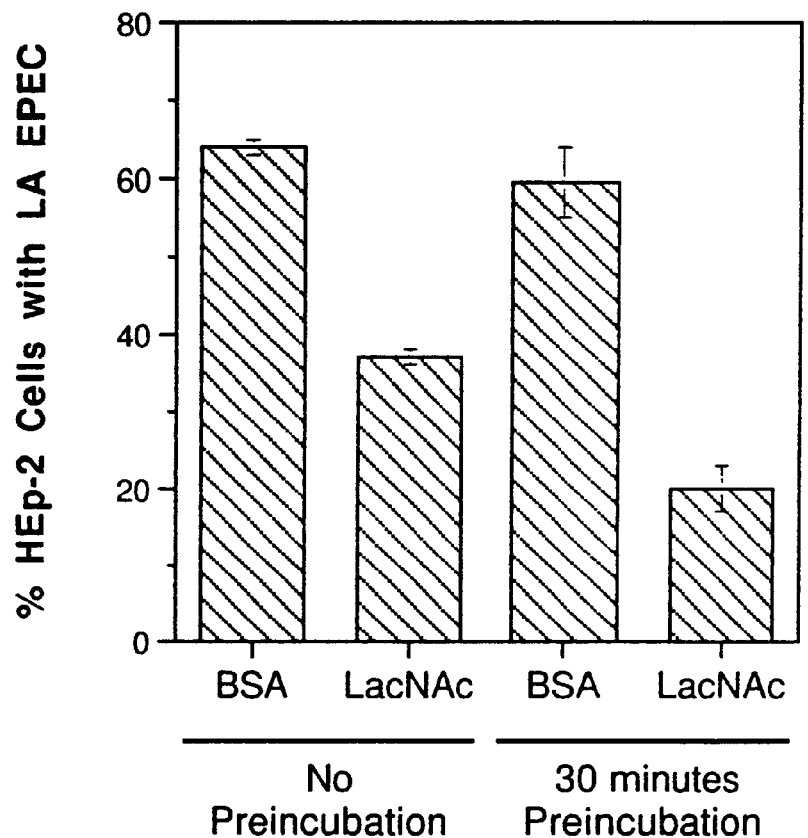
FIG. 3 illustrates the effect of pre-incubation of EPEC with oligosaccharide compositions on EPEC LA. The results show that pre-incubation of the organisms for 30 min with the oligosaccharide LacNAc resulted in reduced LA of EPEC.

The effect of a pre-incubation period on EPEC E2348/69 attachment to HEp-2 cells was determined as follows. Overnight TSB-grown bacteria were grown in DMEM as described earlier. After transferring the bacteria to empty wells of a 96-well plate, LacNAc-BSA (final concentration of 0.6 mg/ml per well) was also added to wells for which the effect of pre-incubation was to be determined. The plate was then incubated in a $CO_2$ incubator for 30 min, after which time LacNAc-BSA was added to the remaining sample wells. The contents of all wells were immediately transferred to wells containing subconfluent HEp-2 cell monolayers and this plate was incubated in a $CO_2$ incubator for 30 min. After washing with PBS, the cells were fixed with methanol and stained with Giemsa stain. HEp-2 cells considered positive for LA EPEC were determined as described earlier. The results shown in FIG. 3 are representative of those obtained in three independent experiments. The error bars represent the range in values for duplicate samples of a single trial.

As shown in FIG. 3, eliminating the pre-incubation step resulted in an approximately two-fold decrease in the inhibitory activity of LacNAc-BSA. Nevertheless, even without the pre-incubation step, LacNAc-BSA reduced EPEC binding to the HEp-2 cells by 42%.

Example 3

Effect of BSA-Glycoconjugates on the Expression of EPEC BfpA and Intimin

The observation that the effectiveness of LacNAc-BSA as an inhibitor of EPEC E2348/69 binding to HEp-2 cells depended on the time of the pre-incubation step was consistent with the assumption that this inhibitor required a finite amount of time to occupy a majority of the adhesin receptor binding domains. It was also possible, however, that during this preincubation period the LacNAc-BSA caused an alteration in the expression of proteins involved in EPEC adherence. To investigate this possibility, we measured the relative expression of BfpA and intimin of EPEC pre-incubated with different glycoconjugates in parallel with binding inhibition experiments.

Figure 4:
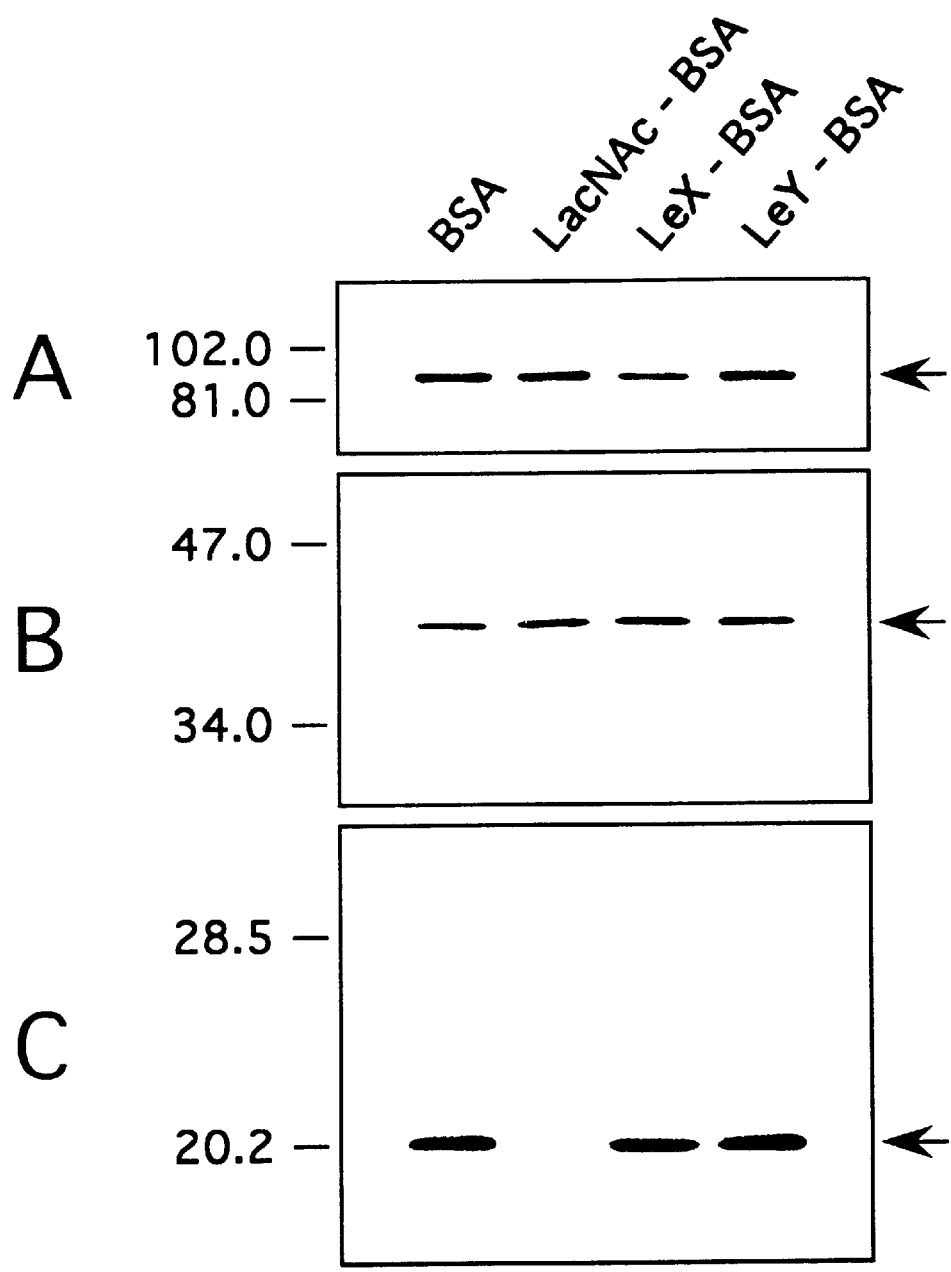
FIG. 4 demonstrates the effect of BSA-glycoconjugates on the expression of EPEC proteins associated with attachment. The glycoconjugates tested decreased expression of the virulence factors BFP and intimin.

The effect of BSA-glycoconjugates on the expression of EPEC proteins associated with attachment was determined as follows. EPEC E2348/69 was cultured in DMEM for 1 h in a $CO_2$ incubator and then transferred to wells of a 48-well plate. After adding BSA-glycoconjugates (0.6 mg/ml final concentration) to these wells, the plate was incubated for an additional 1 h in a $CO_2$ atmosphere. The contents of each well were then transferred to microcentrifuge tubes, washed with PBS, and lysed in sample buffer. Sample proteins were separated by SDS-PAGE (12.5% polyacrylamide) and transferred electrophoretically to Immobilon-P membrane. Bacterial proteins were detected with (A) anti-intimin, (B) anti-maltose-binding protein or (C) anti-BfpA antibodies followed by anti-rabbit peroxidase-conjugated antibodies and the ECL detection system. In FIG. 4, the mobilities of pre-stained molecular size standards (in kilodaltons) are indicated on the left while proteins detected using the antibodies are indicated by arrows on the right.

The results of these experiments demonstrated that the expression of BfpA and intimin were reduced when the bacteria were incubated with specific glycoconjugates (FIG. 4).

The relationship between EPEC binding and BfpA or intimin levels was determined as follows. For each trial, the experiments investigating the effects of various glycoconjugates on bacterial binding and levels of BfpA or intimin were performed in parallel. The assay for EPEC LA to HEp-2 cells was performed as described above. Intimin, maltose-binding protein, and BfpA were detected as described above. After analyzing each of the bands by densitometry, the levels of BfpA and intimin were normalized to the level of maltose-binding protein in each sample. Percentage (y-axis) for each figure refers to the levels of LA, BfpA or intimin of EPEC incubated with specific glyconconjugate(s) relative to that of bacteria cultures in the presence of BSA. Each data point represents a single determination for Trial 1 (Δ), Trial 2 (X) and Trial 3 (●). The over-laying bar graph indicates the mean(s) of the data collected in all trials. LeY-BSA was not used in Trial 1. An analysis of the levels of these proteins by densitometry revealed that BfpA and intimin levels, overall, were decreased to the greatest extent by LacNAc-BSA and LeX-BSA, respectively (FIG. 5).

Example 4

Glyconconjugate Inhibition of EPEC Serotypes O119:H6 and O111:H2

Experiments were performed essentially as described above. After inoculating overnight, tryptic soy broth (TSB)-grown organisms into Dulbecco's modified Eagle medium (DMEM), EPEC O119:H6 or O111:H2 were cultured for 1 h 10 min or 30 min, respectively, at 37° C. in a $CO_2$ incubator. Aliquots of the cultures were then incubated with the BSA-glyconconjugates (final concentration of 0.6 mg/ml) for 30 min before both were transferred to tissue culture plate wells containing sub-confluent HEp-2 cell monolayers. The plates were incubated for an additional 30 min in $CO_2$ incubator, after which time the cells were washed with phosphate-buffered saline (PBS), fixed with methanol, and stained with Giemsa stain.

Figure 8:
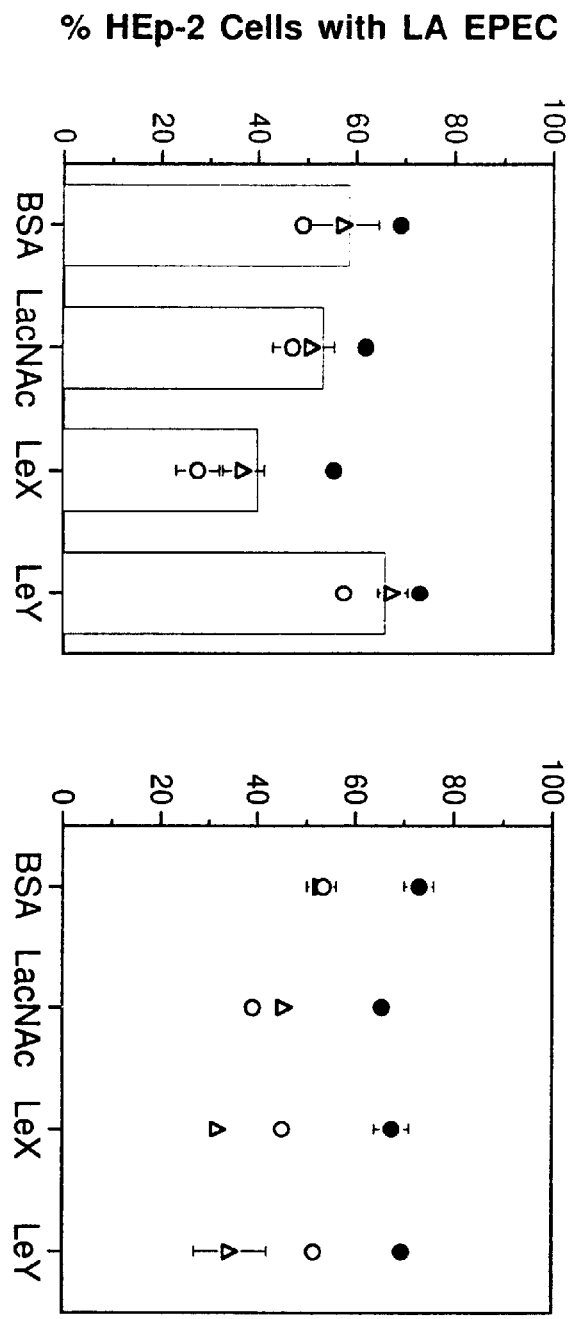
FIG. 8 demonstrates that glycoconjugates reduced the LA of several EPEC serotypes.

The number of HEp-2 cells with LA EPEC was determined as described earlier. The data in FIG. 8 are presented as follows: Trial 1 (●), Trial 2 (○), Trial 3 (Δ). Error bars represent the average of duplicate determinations for each sample. The overlaying bar graph indicates the average of the data obtained from the three independent trials.

Results presented in FIG. 8 showed that EPEC O119:H6 was inhibited to the greatest extent by LeX-BSA, while LacNAc-BSA was the most effective inhibitor of EPEC O111:H2. Nevertheless, all glycoconjugates showed at least 20% LA inhibition for each EPEC serotype tested.

Modification of the above-described modes of carrying out various embodiments of this invention will be apparent to those skilled in the art following the teachings of this invention as set forth herein. The examples described above are not limiting, but are merely exemplary of this invention, the scope of which is defined by the claims which follow.

References

The following references are cited in the application as numbers in brackets ([]) at the relevant portion of the application.

1. Donnenberg, M. S. 1995. Enteropathogenic *Escherichia coli*, p. 709–726. In M. J. Blaser, P. D. Smith, J. I. Ravdin, H. B. Greenberg, and R. L. Guerrant (ed.), Infections of the Gastrointestinal Tract. Raven Press, Ltd., New York.

2. Geyid, A., J. Fletcher, B. A. Gashe, and Ljungh. 1996. Invasion of tissue culture cells by diarrhoeagenic strains of *Escherichia coli* which lack the enteroinvasive inv gene. FEMS Immunol. Med. Microbiol. 14:15–24.
3. Wanke, C. A. 1995. Enteropathogenic and enteroaggregative strains of *Escherichia coli*: clinical features of infection, epidemiology, and pathogenesis. Curr. Clin. Top. Infect. Dis. 15:230–252.
4. Rothbaum, R., A. J. McAdams, R. Giannella, and J. C. Partin. 1982. A clinicopathologic study of enterocyte-adherent *Escherichia coli*: a cause of protracted diarrhea in infants. Gastroenterology. 83:441–454.
5. Barrett, K. E., and K. Dharmsathaphorn. 1991. Secretion and absorption: small intestine and colon, p. 265–294. In T. Yamada, D. H. Alpers, C. Owyang, D. W. Powell, and F. E. Silverstein (ed.), Gastroenterology, vol. 1. J. B. Lippincott Company, Philadelphia, Pa.
6. Fox, S. I. 1987. Human Physiology, Second ed, vol. 1. Wm. C. Brown.
7. Levine, M. M., E. J. Bergquist, D. R. Nalin, D. H. Waterman, R. B. Hornick, C. R. Young, and S. Sotman. 1978. *Escherichia coli* strains that cause diarrhoea but do not produce heat-labile or heat-stable enterotoxins and are non-invasive. Lancet. i:1119–1122.
8. Baldwin, T. J., S. Knutton, R. Haigh, P. H. Williams, H. M. Palmer, A. Aitken, and S. P. Borriello. 1996. Hijacking host cell signal transduction mechanisms during infection with enteropathogenic *Escherichia coli*. Biochem. Soc. Trans. 24:552–558.
9. Ulshen, M. H., and J. L. Rollo. 1980. Pathogenesis of *Escherichia coli* gastroenteritis in man—another mechanism. N. Engl. J. Med. 302:99–101.
10. Clausen, C. R., and D. L. Christie. 1982. Chronic diarrhea in infants caused by adherent enteropathogenic *Escherichia coli*. J. Pediatr. 100:358–61.
11. Moon, H. W., S. C. Whipp, R. A. Argenzio, M. M. Levine, and R. A. Giannella. 1983. Attaching and effacing activities of rabbit and human enteropathogenic *Escherichia coli* in pig and rabbit intestines. Infect. Immun. 41:1340–1351.
12. Donnenberg, M. S., and J. B. Kaper. 1992. Enteropathogenic *Escherichia coli*. Infect. Immun. 60:3953–3961.
13. Hicks, S., G. Frankel, J. B. Kaper, G. Dougan, and A. D. Phillips. 1998. Role of intimin and bundle-forming pili in enteropathogenic *Escherichia coli* adhesion to pediatric intestinal tissue in vitro. Infect. Immun. 66:1570–1578.
14. Cravioto, A., R. J. Gross, S. M. Scotland, and B. Rowe. 1979. An adhesive factor found in strains of *Escherichia coli* belonging to the traditional infantile enteropathogenic serotypes. Curr. Microbiol. 3:95–99.
15. Karch, H., J. Heesemann, R. Laufs, H. P. Kroll, J. B. Kaper, and M. M. Levine. 1987. Serological response to type 1-like somatic fimbriae in diarrheal infection due to classical enteropathogenic *Escherichia coli*. Microb. Pathog. 2:425–434.
16. Scotland, S. M., J. E. Richmond, and B. Rowe. 1983. Adhesion of enteropathogenic strains of *Escherichia coli* (EPEC) to HEp-2 cells is not dependent on the presence of fimbriae. FEMS Microbiol. Lett. 20:191–195.
17. Knutton, S., M. M. Baldini, J. B. Kaper, and A. S. McNeish. 1987. Role of plasmid-encoded adherence factors in adhesion of enteropathogenic *Escherichia coli* to HEp-2 cells. Infect. Immun. 55:78–85.
18. Wadstrom, T., R. A. Adegbola, S. B. Baloda, A. Ljungh, S. K. Sethi, and Y. R. Yuk. 1986. Non-haemagglutinating fimbriae of enteropathogenic *Escherichia coli* (EPEC). Zentralbl. Bakteriol. Hyg. 261:417–424.
19. Yakubu, D. E., D. C. Old, and A. Tavendale. 1991. Production of a mannose-resistant fibrillar haemagglutinin by strains of *Escherichia coli* of EPEC serotype O111:H2. FEMS Microbiol. Lett. 65:233–238.
20. Giron, J. A., A. S. Y. Ho, and G. K. Schoolnik. 1993. Characterization of fimbriae produced by enteropathogenic *Escherichia coli*. J. Bacteriol. 175:7391–7403.
21. Scaletsky, I. C., S. R. Milani, L. R. Trabulsi, and L. R. Travassos. 1988. Isolation and characterization of the localized adherence factor of enteropathogenic *Escherichia coli*. Infect. Immun. 56:2979–2983.
22. Chart, H., and B. Rowe. 1989. The outer membrane protein of enteropathogenic *Escherichia coli*, described as the 'localised adherence factor', is OmpF and probably not involved in adhesion to HEp-2 cells. FEMS Microbiol. Lett. 61:291–296.
23. Scaletsky, I. C. A., M. L. M. Silva, and L. R. Trabulsi. 1984. Distinctive patterns of adherence of enteropathogenic *Escherichia coli* to HeLa cells. Infect. Immun. 45:534–536.
24. Vuopio-Varkila, J., and G. K. Schoolnik. 1991. Localized adherence by enteropathogenic *Escherichia coli* is an inducible phenotype associated with the expression of new outer membrane proteins. J. Exp. Med. 174:1167–1177.
25. Baldini, M. M., J. B. Kaper, M. M. Levine, D. C. A. Candy, and H. W. Moon. 1983. Plasmid-mediated adhesion in enteropathogenic *Escherichia coli*. J. Pediatr. Gastroenterol. Nutr. 2:534–538.
26. Giron, J. A., A. S. Ho, and G. K. Schoolnik. 1991. An inducible bundle-forming pilus of enteropathogenic *Escherichia coli*. Science. 254:710–713.
27. Idota, T., and H. Kawakami. 1995. Inhibitory effects of milk gangliosides on the adhesion of *Escherichia coli* to human intestinal carcinoma cells. Biosci. Biotechnol. Biochem. 59:69–72.
28. Cravioto, A., A. Tello, H. Villafan, J. Ruiz, S. del Vedovo, and J. R. Neeser. 1991. Inhibition of localized adhesion of enteropathogenic *Escherichia coli* to HEp-2 cells by immunoglobulin and oligosaccharide fractions of human colostrum and breast milk. J. Infect. Dis. 163:1247–1255.
29. Jagannatha, H. M., U. K. Sharma, T. Ramaseshan, A. Surolia, and T. S. Balganesh. 1991. Identification of carbohydrate structures as receptors for localised adherent enteropathogenic *Escherichia coli*. Microb. Pathog. 11:259–268.
30. Vanmaele, R. P., M. C. Finlayson, and G. D. Armstrong. 1995. Effect of enteropathogenic *Escherichia coli* on adherent properties of Chinese hamster ovary cells. Infect. Immun. 63:191–198.
31. Deibel, C., S. Kramer, T. Chakraborty, and F. Ebel. 1998. EspE, a novel secreted protein of attaching and effacing bacteria, is directly translocated into infected host cells, where it appears as a tyrosine-phosphorylated 90 kDa protein. Mol. Microbiol. 28:463–474.
32. Kenny, B., R. DeVinney, M. Stein, D. J. Reinscheid, E. A. Frey, and B. B. Finlay. 1997. Enteropathogenic *E.* coli (EPEC) transfers its receptor for intimate adherence into mammalian cells. Cell. 91:511–520.
33. Rosenshine, I., M. S. Donnenberg, J. B. Kaper, and B. B. Finlay. 1992. Signal transduction between enteropathogenic *Escherichia coli* (EPEC) and epithelial cells: EPEC induces tyrosine phosphorylation of host cell proteins to initiate cytoskeletal rearrangement and bacterial uptake. EMBO J. 11:3551–3560.
34. Rosenshine, I., S. Ruschkowski, M. Stein, D. J. Reinscheid, S. D. Mills, and B. B. Finlay. 1996. A pathogenic bacterium triggers epithelial signals to form a functional bacterial receptor that mediates actin pseudopod formation. EMBO J. 15:2613–2624.
35. Jerse, A. E., and J. B. Kaper. 1991. The eae gene of enteropathogenic *Escherichia coli* encodes a 94-kilodalton membrane protein, the expression of which is influenced by the EAF plasmid. Infect. Immun. 59:4302–4309.
36. Jerse, A. E., J. Yu, B. D. Tall, and J. B. Kaper. 1990. A genetic locus of enteropathogenic *Escherichia coli* necessary for the production of attaching and effacing lesions on tissue culture cells. Proc. Natl. Acad. Sci. USA. 87:7839–7843.
37. AduBobie, J., G. Frankel, C. Bain, A. G. Goncalves, L. R. Trabulsi, G. Douce, S. Knutton, and G. Dougan. 1998. Detection of intimins alpha, beta, gamma, and delta, four intimin derivatives expressed by attaching and effacing microbial pathogens. J. Clin. Microbiol. 36:662–668.
38. Agin, T. S., and M. K. Wolf. 1997. Identification of a family of intimins common to *Escherichia coli* causing attaching-effacing lesions in rabbits, humans, and swine. Infect. Immun. 65:320–6.
39. Frankel, G., D. C. A. Candy, P. Everest, and G. Dougan. 1994. Characterization of the C-terminal domains of intimin-like proteins of enteropathogenic and enterohemorrhagic *Escherichia coli, Citrobacter freundii,* and *Hafnia alvei*. Infect. Immun. 62:1835–1842.
40. Knutton, S., J. AduBobie, C. Bain, A. D. Phillips, G. Dougan, and G. Frankel. 1997. Down regulation of intimin expression during attaching and effacing enteropathogenic *Escherichia coli* adhesion. Infect. Immun. 65:1644–1652.
41. Chart, H., S. M. Scotland, G. A. Willshaw, and B. Rowe. 1988. HEp-2 adhesion and the expression of a 94 kDa outer-membrane protein by strains of *Escherichia coli* belonging to enteropathogenic serogroups. J. Gen. Microbiol. 134:1315–1321.
42. Vanmaele, R. P., and G. D. Armstrong. 1997. Effect of carbon source on localized adherence of enteropathogenic *Escherichia coli*. Infect. Immun. 65:1408–1413.
43. Haigh, R., T. Baldwin, S. Knutton, and P. H. Williams. 1995. Carbon dioxide regulated secretion of the EaeB protein of enteropathogenic *Escherichia coli* . FEMS Microbiol. Lett. 129:63–67.
44. Kenny, B., A. Abe, M. Stein, and B. B. Finlay. 1997. Enteropathogenic *Escherichia coli* protein secretion is induced in response to conditions similar to those in the gastrointestinal tract. Infect. Immun. 65:2606–2612.
45. Puente, J. L., D. Bieber, S. W. Ramer, W. Murray, and G. K. Schoolnik. 1996. The bundle-forming pili of enteropathogenic *Escherichia coli:* Transcriptional regulation by environmental signals. Mol. Microbiol. 20:87–100.
46. Rosenshine, I., S. Ruschkowski, and B. B. Finlay. 1996. Expression of attaching effacing activity by enteropathogenic *Escherichia coli* depends on growth phase, temperature, and protein synthesis upon contact with epithelial cells. Infect. Immun. 64:966–973.
47. Stone, K. D., H. Z. Zhang, L. K. Carlson, and M. S. Donnenberg. 1996. A cluster of fourteen genes from enteropathogenic *Escherichia coli* is sufficient for the biogenesis of a type IV pilus. Mol. Microbiol. 20:325–337.
48. Jerse, A. E., W. C. Martin, J. E. Galen, and J. B. Kaper. 1990. Oligonucleotide probe for detection of the enteropathogenic *Escherichia coli* (EPEC) adherence factor of localized adherent EPEC. J. Clin. Microbiol. 28:2842–2844.
49. Frankel, G., O. Lider, R. Hershkoviz, A. P. Mould, S. G. Kachalsky, D. C. A. Candy, L. Cahalon, M. J. Humphries, and G. Dougan. 1996. The cell-binding domain of intimin from enteropathogenic *Escherichia coli* binds to beta1 integrins. J. Biol. Chem. 271:20359–20364.
50. Kenny, B., and B. B. Finlay. 1995. Protein secretion by enteropathogenic *Escherichia coli* is essential for transducing signals to epithelial cells. Proc. Natl. Acad. Sci. USA. 92:7991–7995.
51. Prieto, P. A., R. D. Larsen, M. Cho, H. N. Rivera, A. Shilatifard, J. B. Lowe, R. D. Cummings, and D. F. Smith. 1997. Expression of human H-type alpha1,2-fucosyltransferase encoding for blood group H(O) antigen in Chinese hamster ovary cells. J. Biol. Chem. 272:2089–2097.
52. Donnenberg, M. S., J. A. Giron, J. P. Nataro, and J. B. Kaper. 1992. A plasmid-encoded type IV fimbrial gene of enteropathogenic *Escherichia coli* associated with localized adherence. Mol. Microbiol. 6:3427–3437.
53. Knutton, S., T. Baldwin, P. H. Williams, and A. S. McNeish. 1989. Actin accumulation at sites of bacterial adhesion to tissue culture cells: basis of a new diagnostic test for enteropathogenic and enterohemorrhagic *Escherichia coli*. Infect. Immun. 57:1290–1298.
54. Finne, J., M. E. Breimer, G. C. Hansson, K. A. Karlsson, H. Leffler, J. F. G. Vliegenthart, and H. van Halbeek. 1989. Novel polyfucosylated N-linked glycopeptides with blood group A, H, X, and Y determinants from human small intestinal epithelial cells. J. Biol. Chem. 264:5720–5735.
55. Karlsson, K. A. 1998. Meaning and therapeutic potential of microbial recognition of host glycconjugates. Mol. Microbiol. 29:1–11.
56. Zopf, D., and S. Roth. 1996. Oligosaccharide antiinfective agents. Lancet. 347:1017–1021.
57. Jarvis, K. G., J. A. Giron, A. E. Jerse, T. K. McDaniel, M. S. Donnenberg, and J. B. Kaper. 1995. Enteropathogenic *Escherichia coli* contains a putative type III secretion system necessary for the export of proteins involved in attaching and effacing lesion formation. Proc. Natl. Acad. Sci. USA. 92:7996–8000.
58. Lee, C. A. 1997. Type III secretion systems: machines to deliver bacterial proteins into eukaryotic cells? Trends Microbiol. 5:148–56.
59. Francis, D. H., J. E. Collins, and J. R. Duimstra. 1986. Infection of gnotobiotic pigs with an *Escherichia coli* O157:H7 strain associated with an outbreak of hemorrhagic colitis. Infect. Immun. 51:953–956.
60. Tzipori, S., I. K. Wachsmuth, C. Chapman, R. Birden, J. Brittingham, C. Jackson, and J. Hogg. 1986. The pathogenesis of hemorrhagic colitis caused by *Escherichia coli* O157:H7 in gnotobiotic piglets. J. Infect. Dis. 154:712–6.
61. Albert, M. J., K. Alam, M. Islam, J. Montanaro, A. S. Rahaman, K. Haider, M. A. Hossain, A. K. Kibriya, and S. Tzipori. 1991. *Hafnia alvei*, a probable cause of diarrhea in humans. Infect. Immun. 59:1507–1513.
62. Beebakhee, G., M. Louie, J. De Azavedo, and J. Brunton. 1992. Cloning and nucleotide sequence of the eae gene homologue from enterohemorrhagic *Escherichia coli* serotype O157:H7. FEMS Microbiol. Lett. 70:63–68.
63. Schauer, D. B., and S. Falkow. 1993. Attaching and effacing locus of a *Citrobacter freundii* biotype that causes transmissible murine colonic hyperplasia. Infect. Immun. 61:2486–2492.
64. Yu, J., and J. B. Kaper. 1992. Cloning and characterization of the eae gene of enterohaemorrhagic *Escherichia coli* O157:H7. Mol. Microbiol. 6:411–417.
65. Lemieux, R. U., D. R. Bundle, and D. A. Baker. 1975. The 1) properties of a "synthetic" antigen related to the human blood-group Lewis a. J. Am. Chem. Soc. 97:4076–4083.
66. Zhang, H. Z., and M. S. Donnenberg. 1996. DsbA is required for stability of the type IV pilin of enteropathogenic *Escherichia coli*. Mol. Microbiol. 21:787–797.
67. Laemmli, U. K. 1970. Cleavage of structural proteins during the assembly of the head of bacteriophage T4. Nature. 227:680–5.
68. Donnenberg, M. S., S. B. Calderwood, A. Donohue Rolfe, G. T. Keusch, and J. B. Kaper. 1990. Construction and analysis of TnphoA mutants of enteropathogenic *Escherichia coli* unable to invade HEp-2 cells. Infect. Immun. 58:1565–1571.
69. Ashkenazi, S. 1994. A review of the effect of human milk fractions on the adherence of diarrheogenic *Escherichia coli* to the gut in an animal model. Isr. J. Med. Sci. 30:335–338.
70. Eden, C. S., R. Freter, L. Hagberg, R. Hull, H. Leffler, and G. Schoolnik. 1982. Inhibition of experimental ascending urinary tract infection by an epithelial cell-surface receptor analogue. Nature. 298:560–562.
71. Kenny, B., L. C. Lai, B. B. Finlay, and M. S. Donnenberg. 1996. EspA, a protein secreted by enteropathogenic *Escherichia coli*, is required to induce signals in epithelial cells. Mol. Microbiol. 20:313–323.
72. Knutton, S., I. Rosenshine, M. J. Pallen, I. Nisan, B. C. Neves, C. Bain, C. Wolff, G. Dougan, and G. Frankel. 1998. A novel EspA-associated surface organelle of enteropathogenic *Escherichia coli* involved in protein translocation into epithelial cells. EMBO J. 17:2166–2176.
73. Lai, L. C., L. A. Wainwright, K. D. Stone, and M. S. Donnenberg. 1997. A third secreted protein that is encoded by the enteropathogenic *Escherichia coli* pathogenicity island is required for transduction of signals and for attaching and effacing activities in host cells. Infect. Immun. 65:2211–2217.
74. Sohel, I., J. L. Puente, S. W. Ramer, D. Bieber, C. Y. Wu, and G. K. Schoolnik. 1996. Enteropathogenic *Escherichia coli*: identification of a gene cluster coding for bundle-forming pilus morphogenesis. J. Bacteriol. 178:2613–2628.
75. Mouricourt, M. 1991. Swine and cattle enterotoxigenic *Escherichia coli*—mediated diarrhea. Development of therapies based on inhibition of bacteria-host interactions. Eur. J. Epidemiol. 7:588–604.
76. Simon, P. M., P. L. Goode, A. Mobasseri, and D. Zopf. 1997. Inhibition of *Helicobacter pylori* binding to gastrointestinal epithelial cells by sialic acid-containing oligosaccharides. Infect. Immun. 65:750–757.

The disclosure of the above publications, patents and patent applications and any publication, patent or patent application referred to in the specification of this application are herein incorporated by reference in their entirety to the same extent as if the language of each individual publication, patent and patent application were specifically and individually included herein.

What is claimed is:

1. A method to reduce the virulence of an EPEC organism, which method comprises contacting an EPEC organism which expresses virulence factors with an amount of a composition effective to reduce the expression of virulence factors of said organism, said composition comprising a monosaccharide or an oligosaccharide sequence, wherein said monosaccharide or oligosaccharide causes at least a 20% decrease in localized adherence of said organism.

2. The method of claim 1 wherein said monosaccharide or oligosaccharide sequence has from 1 to 5 saccharide units.

3. The method of claim 1 wherein said monosaccharide or oligosaccharide sequence is selected from the group consisting of LacNAc, LeX and LeY.

4. The method of claim 1 wherein said monosaccharide or oligosaccharide sequence is attached to a pharmaceutically acceptable support.

5. The method of claim 4 wherein said monosaccharide or oligosaccharide sequence is covalently attached to a pharmaceutically acceptable support through a non-peptidyl compatible linker arm.

6. The method of claim 5 wherein said linker arm is —$(CH_2)_8C(O)$—.

7. The method of claim 1 wherein said monosaccharide or oligosaccharide sequence is effective in reducing the virulence of at least two EPEC serotypes.

8. The method of claim 1, wherein said contact is effected in the gut of a subject with an EPEC infection.

9. A composition useful for reducing the virulence of an EPEC organism, which composition comprises a monosaccharide or an oligosaccharide sequence which reduces the expression of virulence factors by EPEC.

10. The composition of claim 9 wherein said monosaccharide or oligosaccharide sequence has from 1 to 5 saccharide units.

11. The composition of claim 9 wherein said monosaccharide or oligosaccharide sequence is selected from the group consisting of LacNAc, LeX and LeY.

12. The composition of claim 9 wherein said monosaccharide or oligosaccharide sequence is attached to a pharmaceutically acceptable support.

13. The composition of claim 12 wherein said monosaccharide or oligosaccharide sequence is covalently attached to a pharmaceutically acceptable support through a non-peptidyl compatible linker arm.

14. The composition of claim 13 wherein said linker arm is —$(CH_2)_8C(O)$—.

15. The composition of claim 9 wherein said monosaccharide or oligosaccharide sequence is effective in reducing the virulence of at least two EPEC serotypes.

16. The composition of claim 9, wherein said virulence factors are selected from the group consisting of bundle-forming pili and intimin.

17. A composition useful for reducing the virulence of an EPEC organism, which composition comprises a monosaccharide or an oligosaccharide sequence which causes at least a 20% decrease in localized adherence of EPEC.

18. The composition of claim 17 wherein said monosaccharide or oligosaccharide sequence has from 1 to 5 saccharide units.

19. The composition of claim 17 wherein said monosaccharide or oligosaccharide sequence is selected from the group consisting of LacNAc, LeX and LeY.

20. The composition of claim 17 wherein said monosaccharide or oligosaccharide sequence is attached to a pharmaceutically acceptable support.

21. The composition of claim 17 wherein said monosaccharide or oligosaccharide sequence is covalently attached to a pharmaceutically acceptable support through a non-peptidyl compatible linker arm.

22. The composition of claim 21 wherein said linker is $-(CH_2)_8C(O)-$.

23. The composition of claim 17 wherein said monosaccharide or oligosaccharide sequence is effective in reducing the virulence of at least two EPEC serotypes.

* * * * *